US012731683B2

(12) United States Patent
Kohlbrecher et al.

(10) Patent No.: US 12,731,683 B2
(45) **Date of Patent: *Sep. 8, 2026**

(54) MEDICAL DEVICE SYSTEM PERFORMANCE INDEX

(71) Applicant: ICU Medical, Inc., San Clemente, CA (US)

(72) Inventors: Christopher Egan Kohlbrecher, Poway, CA (US); Jonathan Leigh Walton, Escondido, CA (US); Daniel Chien-Yu Hsu, San Diego, CA (US); Michael Paul Myers, San Diego, CA (US)

(73) Assignee: ICU Medical, Inc., San Clemente, CA (US)

( * ) Notice: Subject to any disclaimer, the term of this patent is extended or adjusted under 35 U.S.C. 154(b) by 790 days.

This patent is subject to a terminal disclaimer.

(21) Appl. No.: 18/053,511

(22) Filed: Nov. 8, 2022

(65) Prior Publication Data

US 2023/0139360 A1 May 4, 2023

Related U.S. Application Data

(63) Continuation of application No. 16/385,746, filed on Apr. 16, 2019, now Pat. No. 11,501,877, which is a (Continued)

(51) Int. Cl.
*G16H 40/63* (2018.01)
*A61M 5/142* (2006.01)
(Continued)

(52) U.S. Cl.
CPC ......... *G16H 40/63* (2018.01); *G06F 11/3006* (2013.01); *G06F 11/3409* (2013.01);
(Continued)

(58) Field of Classification Search
CPC ........ G16H 40/63; G16H 10/60; G16H 40/40; G16H 70/20; G16H 20/17; G06F 11/3006;
(Continued)

(56) References Cited

U.S. PATENT DOCUMENTS 4,024,864 A 5/1977 Davies et al.
4,055,175 A 10/1977 Clemens et al.
(Continued)

FOREIGN PATENT DOCUMENTS

AU 2004226440 10/2004
AU 2004305087 7/2005
(Continued)

OTHER PUBLICATIONS

Amano, Hikaru, et al. "A remote drip infusion monitoring system employing Bluetooth." 2012 Annual International Conference of the IEEE Engineering in Medicine and Biology Society. IEEE, 2012. (Year: 2012).*

(Continued)

*Primary Examiner* — Jesse P Frumkin
(74) *Attorney, Agent, or Firm* — Knobbe, Martens, Olson & Bear, LLP

(57) ABSTRACT

A distributed network system and method includes a processing unit configured to manage safety data for a plurality of medical devices, a database software component in communication with the processing unit, and a monitoring software component in communication with the processing unit. The monitoring software component is configured to monitor a number of messages between a number of medical devices and the processing unit, to process performance parameters to generate an overall performance index, and to generate an output that is viewable by a user. The output includes relative contributions of each of the performance
(Continued)

parameters to the overall performance index, where the overall performance index is generated using a weighting factor associated with each of the performance parameters. The performance parameters include the number of messages waiting to be processed, which has the largest weighting factor, and a disk queue length, which has the smallest weighting factor.

20 Claims, 8 Drawing Sheets

Related U.S. Application Data continuation of application No. 14/538,545, filed on Nov. 11, 2014, now Pat. No. 10,311,972.

(60) Provisional application No. 61/902,504, filed on Nov. 11, 2013.

(51) Int. Cl.
*G06F 11/30* (2006.01)
*G06F 11/34* (2006.01)
*G16H 10/60* (2018.01)
*G16H 20/17* (2018.01)
*G16H 40/40* (2018.01)
*G16H 70/20* (2018.01)

(52) U.S. Cl.
CPC ............. *G16H 10/60* (2018.01); *G16H 40/40* (2018.01); *G16H 70/20* (2018.01); *A61M 5/142* (2013.01); *G06F 11/3065* (2013.01); *G06F 11/3442* (2013.01); *G06F 11/3452* (2013.01); *G06F 11/3457* (2013.01); *G16H 20/17* (2018.01)

(58) Field of Classification Search
CPC ............. G06F 11/3409; G06F 11/3065; G06F 11/3442; G06F 11/3452; G06F 11/3457; A61M 5/142
See application file for complete search history.

(56) References Cited

U.S. PATENT DOCUMENTS 4,151,845 A 5/1979 Clemens
4,213,454 A 7/1980 Shim
4,240,438 A 12/1980 Updike et al.
4,280,494 A 7/1981 Cosgrove et al.
4,308,866 A 1/1982 Jeliffe
4,370,983 A 2/1983 Lichtenstein et al.
4,373,527 A 2/1983 Fischell
4,392,849 A 7/1983 Petre et al.
4,395,259 A 7/1983 Prestele et al.
4,457,751 A 7/1984 Rodler
4,464,170 A 8/1984 Clemens
4,469,481 A 9/1984 Kobayashi
4,475,901 A 10/1984 Kraegen et al.
4,494,950 A 1/1985 Fischell
4,498,843 A 2/1985 Schneider et al.
4,515,584 A 5/1985 Abe et al.
4,526,568 A 7/1985 Clemens et al.
4,529,401 A 7/1985 Leslie et al.
4,543,955 A 10/1985 Schroeppel
4,551,133 A 11/1985 Zegers de Beyl et al.
4,553,958 A 11/1985 LeCocq
4,559,037 A 12/1985 Franetzki et al.
4,613,937 A 9/1986 Batty
4,624,661 A 11/1986 Arimond
4,633,878 A 1/1987 Bombardieri
4,634,426 A 1/1987 Kamen
4,634,427 A 1/1987 Hannula et al.
4,674,652 A 6/1987 Aten et al.
4,676,776 A 6/1987 Howson et al.
4,679,562 A 7/1987 Luksha
4,685,903 A 8/1987 Cable et al.
4,695,954 A 9/1987 Rose
4,696,671 A 9/1987 Epstein et al.
4,714,462 A 12/1987 DiDomenico
4,722,734 A 2/1988 Kolin
4,730,849 A 3/1988 Siegel
4,731,051 A 3/1988 Fischell
4,741,732 A 5/1988 Crankshaw et al.
4,756,706 A 7/1988 Kerns et al.
4,776,842 A 10/1988 Franetzki et al.
4,785,969 A 11/1988 McLaughlin
4,803,625 A 2/1989 Fu et al.
4,835,372 A 5/1989 Gombrich et al.
4,838,275 A 6/1989 Lee
4,838,856 A 6/1989 Mulreany et al.
4,838,857 A 6/1989 Strowe et al.
4,854,324 A 8/1989 Hirschman et al.
4,857,716 A 8/1989 Gombrich et al.
4,858,154 A 8/1989 Anderson et al.
4,898,578 A 2/1990 Rubalcaba, Jr.
4,908,017 A 3/1990 Howson et al.
4,933,873 A 6/1990 Kaufman et al.
4,943,279 A 7/1990 Samiotes et al.
4,946,439 A 8/1990 Eggers
4,953,745 A 9/1990 Rowlett
4,978,335 A 12/1990 Arthur, III
5,000,739 A 3/1991 Kulisz et al.
5,010,473 A 4/1991 Jacobs
5,014,698 A 5/1991 Cohen
5,016,172 A 5/1991 Dessertine
5,026,084 A 6/1991 Paisfield
5,034,004 A 7/1991 Crankshaw
5,041,086 A 8/1991 Koenig et al.
5,058,161 A 10/1991 Weiss
5,078,683 A 1/1992 Sancoff et al.
5,084,828 A 1/1992 Kaufman et al.
5,088,981 A 2/1992 Howson et al.
5,097,505 A 3/1992 Weiss
5,100,380 A 3/1992 Epstein et al.
5,102,392 A 4/1992 Sakai et al.
5,104,374 A 4/1992 Bishko et al.
5,109,850 A 5/1992 Blanco et al.
5,131,816 A 7/1992 Brown
5,142,484 A 8/1992 Kaufman et al.
5,153,827 A 10/1992 Coutre et al.
5,157,640 A 10/1992 Backner
5,161,222 A 11/1992 Montejo et al.
5,177,993 A 1/1993 Beckman et al.
5,181,910 A 1/1993 Scanlon
5,190,522 A 3/1993 Wocicki et al.
5,199,439 A 4/1993 Zimmerman et al.
5,200,891 A 4/1993 Kehr et al.
5,216,597 A 6/1993 Beckers
5,221,268 A 6/1993 Barton et al.
5,230,061 A 7/1993 Welch
5,243,982 A 9/1993 Möstl et al.
5,244,463 A 9/1993 Cordner, Jr. et al.
5,249,260 A 9/1993 Nigawara et al.
5,254,096 A 10/1993 Rondelet et al.
5,256,156 A 10/1993 Kern et al.
5,256,157 A 10/1993 Samiotes et al.
5,261,702 A 11/1993 Mayfield
5,317,506 A 5/1994 Coutre et al.
5,319,355 A 6/1994 Russek
5,319,363 A 6/1994 Welch et al.
5,330,634 A 7/1994 Wong et al.
5,338,157 A * 8/1994 Blomquist ............ G16H 20/17 417/63
5,341,476 A 8/1994 Lowell
5,364,346 A 11/1994 Schrezenmeir
5,366,346 A 11/1994 Danby
5,368,562 A 11/1994 Blomquist et al.
5,373,454 A 12/1994 Kanda et al.
5,376,070 A 12/1994 Purvis et al.
5,378,231 A 1/1995 Johnson et al.
5,389,071 A 2/1995 Kawahara et al.
5,389,078 A 2/1995 Zalesky et al.

(56) References Cited

U.S. PATENT DOCUMENTS 5,417,222 A 5/1995 Dempsey et al.
5,423,748 A 6/1995 Uhala
5,429,602 A 7/1995 Hauser
5,431,627 A 7/1995 Pastrone et al.
5,432,777 A 7/1995 Le Boudec et al.
5,445,621 A 8/1995 Poli et al.
5,447,164 A 9/1995 Shaya et al.
5,455,851 A 10/1995 Chaco et al.
5,461,365 A 10/1995 Schlager et al.
5,464,392 A 11/1995 Epstein et al.
5,465,082 A 11/1995 Chaco
5,485,408 A 1/1996 Blomquist
5,486,286 A 1/1996 Peterson et al.
5,493,430 A 2/1996 Lu et al.
5,496,273 A 3/1996 Pastrone et al.
5,505,828 A 4/1996 Wong et al.
5,507,288 A 4/1996 Bocker et al.
5,507,786 A 4/1996 Morgan et al.
5,508,499 A 4/1996 Ferrario
5,515,713 A 5/1996 Saugues et al.
5,520,637 A 5/1996 Pager et al.
5,522,798 A 6/1996 Johnson et al.
5,547,470 A 8/1996 Johnson et al.
5,554,013 A 9/1996 Owens et al.
5,562,615 A 10/1996 Nassif
5,577,169 A 11/1996 Prezioso
5,582,323 A 12/1996 Kurtenbach
5,582,593 A 12/1996 Hultman
5,594,786 A 1/1997 Chaco et al.
5,598,519 A 1/1997 Narayanan
5,620,608 A 4/1997 Rosa et al.
5,630,710 A 5/1997 Tune et al.
5,636,044 A 6/1997 Yuan et al.
5,643,212 A 7/1997 Coutre et al.
5,651,775 A 7/1997 Walker et al.
5,658,131 A 8/1997 Aoki et al.
5,658,250 A 8/1997 Blomquist et al.
5,665,065 A 9/1997 Colman et al.
5,669,877 A 9/1997 Blomquist
5,672,154 A 9/1997 Sillén et al.
5,681,285 A 10/1997 Ford et al.
5,685,844 A 11/1997 Marttila
5,687,717 A 11/1997 Halpern et al.
5,689,229 A 11/1997 Chaco et al.
5,697,899 A 12/1997 Hillman et al.
5,699,509 A 12/1997 Gary et al.
5,708,714 A 1/1998 Lopez et al.
5,713,350 A 2/1998 Yokota et al.
5,713,856 A 2/1998 Eggers et al.
5,718,562 A 2/1998 Lawless et al.
5,719,761 A 2/1998 Gatti et al.
5,733,259 A 3/1998 Valcke et al.
5,738,102 A 4/1998 Lemelson
5,744,027 A 4/1998 Connell et al.
5,752,621 A 5/1998 Passamante
5,754,111 A 5/1998 Garcia
5,764,034 A 6/1998 Bowman et al.
5,764,159 A 6/1998 Neftel et al.
5,772,635 A 6/1998 Dastur et al.
5,774,865 A 6/1998 Glynn
5,778,256 A 7/1998 Darbee
5,778,345 A 7/1998 McCartney
5,781,442 A 7/1998 Engleson et al.
5,782,805 A 7/1998 Meinzer et al.
5,788,669 A 8/1998 Peterson
5,797,515 A 8/1998 Liff et al.
5,800,387 A 9/1998 Duffy et al.
5,814,015 A 9/1998 Gargano et al.
5,822,544 A 10/1998 Chaco et al.
5,822,715 A 10/1998 Worthington et al.
5,827,179 A 10/1998 Lichter et al.
5,832,448 A 11/1998 Brown
5,836,910 A 11/1998 Duffy et al.
5,850,344 A 12/1998 Conkright
5,867,821 A 2/1999 Ballantyne et al.
5,870,733 A 2/1999 Bass et al.
5,871,465 A 2/1999 Vasko
5,873,731 A 2/1999 Predergast
5,885,245 A 3/1999 Lynch et al.
5,897,493 A 4/1999 Brown
5,897,498 A 4/1999 Canfield, II et al.
5,910,252 A 6/1999 Truitt et al.
5,912,818 A 6/1999 McGrady et al.
5,915,240 A 6/1999 Karpf
5,920,054 A 7/1999 Uber, III
5,920,263 A 7/1999 Huttenhoff et al.
5,924,074 A 7/1999 Evans
5,931,764 A 8/1999 Freeman et al.
5,935,099 A 8/1999 Peterson et al.
5,935,106 A 8/1999 Olsen
5,941,846 A 8/1999 Duffy et al.
5,956,501 A 9/1999 Brown
5,957,885 A 9/1999 Bollish et al.
5,960,085 A 9/1999 de la Huerga
5,961,448 A 10/1999 Swenson et al.
5,967,559 A 10/1999 Abramowitz
5,971,594 A 10/1999 Sahai et al.
5,975,081 A 11/1999 Hood et al.
5,990,838 A 11/1999 Burns et al.
5,997,476 A 12/1999 Brown
6,000,828 A 12/1999 Leet
6,003,006 A 12/1999 Colella et al.
6,012,034 A 1/2000 Hamparian et al.
6,017,318 A 1/2000 Gauthier et al.
6,021,392 A 2/2000 Lester et al.
6,024,539 A 2/2000 Blomquist
6,024,699 A 2/2000 Surwit et al.
6,032,155 A 2/2000 de la Huerga
6,032,676 A 3/2000 Moore
6,039,251 A 3/2000 Holowko et al.
6,070,761 A 6/2000 Bloom et al.
6,073,106 A 6/2000 Rozen et al.
6,104,295 A 8/2000 Gaisser et al.
6,112,182 A 8/2000 Akers et al.
6,112,323 A 8/2000 Meizlik et al.
RE36,871 E 9/2000 Epstein et al.
6,115,365 A 9/2000 Newberg
6,115,390 A 9/2000 Chuah
6,122,536 A 9/2000 Sun et al.
6,126,637 A 10/2000 Kriesel et al.
6,135,949 A 10/2000 Russo et al.
6,150,942 A 11/2000 O'Brien
6,151,643 A 11/2000 Cheng et al.
6,157,914 A 12/2000 Seto et al.
6,159,147 A 12/2000 Lichter et al.
6,167,567 A 12/2000 Chiles et al.
6,182,667 B1 2/2001 Hanks et al.
6,189,105 B1 2/2001 Lopes
6,195,589 B1 2/2001 Ketcham
6,208,974 B1 3/2001 Campbell et al.
6,222,323 B1 4/2001 Yamashita et al.
6,223,440 B1 5/2001 Rashman
6,226,277 B1 5/2001 Chuah
6,227,371 B1 5/2001 Song
6,234,176 B1 5/2001 Domae et al.
6,241,704 B1 6/2001 Peterson et al.
6,248,067 B1 6/2001 Causey, III et al.
6,249,705 B1 6/2001 Snell
6,257,265 B1 7/2001 Brunner et al.
6,259,355 B1 7/2001 Chaco et al.
6,269,340 B1 7/2001 Ford et al.
6,270,455 B1 8/2001 Brown
6,271,813 B1 8/2001 Palalau
6,277,072 B1 8/2001 Bardy
6,280,380 B1 8/2001 Bardy
6,283,761 B1 9/2001 Joao
6,285,665 B1 9/2001 Chuah
6,292,860 B1 9/2001 Cochcroft, Jr.
6,312,378 B1 11/2001 Bardy
6,327,254 B1 12/2001 Chuah
6,330,008 B1 12/2001 Razdow et al.
6,339,718 B1 1/2002 Zatezalo et al.
6,346,886 B1 2/2002 de la Huerga
6,363,282 B1 3/2002 Nichols et al.

(56) References Cited

U.S. PATENT DOCUMENTS 6,371,719 B1 4/2002 Hildebrandt
6,377,548 B1 4/2002 Chuah
6,388,951 B1 5/2002 Matsumoto et al.
6,406,426 B1 6/2002 Reuss et al.
6,408,330 B1 6/2002 de la Huerga
6,418,334 B1 7/2002 Unger et al.
6,427,088 B1 7/2002 Bowman et al.
6,428,483 B1 8/2002 Carlebach
6,442,432 B2 8/2002 Lee
6,469,991 B1 10/2002 Chuah
6,475,180 B2 11/2002 Peterson et al.
6,482,158 B2 11/2002 Mault
6,485,418 B2 11/2002 Yasushi et al.
6,494,694 B2 12/2002 Lawless et al.
6,494,831 B1 12/2002 Koritzinsky
6,497,680 B1 12/2002 Holst et al.
6,514,460 B1 2/2003 Fendrock
6,517,482 B1 2/2003 Eiden et al.
6,519,569 B1 2/2003 White et al.
6,520,930 B2 2/2003 Critchlow et al.
6,540,672 B1 4/2003 Simonsen et al.
6,542,902 B2 4/2003 Dulong et al.
6,544,212 B2 4/2003 Galley et al.
6,544,228 B1 4/2003 Heitmeier
6,546,350 B1 4/2003 Hartmann et al.
6,551,276 B1 4/2003 Mann et al.
6,554,798 B1 4/2003 Mann et al.
6,558,320 B1 5/2003 Causey et al.
6,558,351 B1 5/2003 Steil et al.
6,565,509 B1 5/2003 Say et al.
6,567,416 B1 5/2003 Chuah
6,571,294 B2 5/2003 Simmon et al.
6,572,542 B1 6/2003 Houben et al.
6,572,545 B2 6/2003 Knobbe et al.
6,578,002 B1 6/2003 Derzay et al.
6,581,117 B1 6/2003 Klein et al.
6,587,034 B1 7/2003 Heiman et al.
6,589,229 B1 7/2003 Connelly et al.
6,599,281 B1 7/2003 Struys et al.
6,602,191 B2 8/2003 Quy
6,605,072 B2 8/2003 Struys et al.
6,628,809 B1 9/2003 Rowe et al.
6,631,353 B1 10/2003 Davis et al.
6,640,246 B1 10/2003 Gardy, Jr. et al.
6,641,533 B2 11/2003 Causey, III et al.
6,647,299 B2 11/2003 Bourget
6,652,455 B1 11/2003 Kocher
6,653,937 B2 11/2003 Nelson et al.
6,659,947 B1 12/2003 Carter et al.
6,669,630 B1 12/2003 Joliat et al.
6,671,563 B1 12/2003 Engleson et al.
6,673,033 B1 1/2004 Sciulli et al.
6,674,403 B2 1/2004 Gray et al.
6,681,003 B2 1/2004 Linder et al.
6,689,091 B2 2/2004 Bui et al.
6,692,241 B2 2/2004 Watanabe et al.
6,694,191 B2 2/2004 Starkweather et al.
6,694,334 B2 2/2004 DuLong et al.
6,721,286 B1 4/2004 Williams et al.
6,721,582 B2 4/2004 Trepagnier et al.
6,725,200 B1 4/2004 Rost
6,731,989 B2 5/2004 Engleson et al.
6,740,072 B2 5/2004 Starkweather et al.
6,751,651 B2 6/2004 Crockett
6,752,787 B1 6/2004 Causey, III et al.
6,753,830 B2 6/2004 Gelbman
6,758,810 B2 7/2004 Lebel et al.
6,773,396 B2 8/2004 Flach et al.
6,774,786 B1 8/2004 Havekost et al.
6,775,577 B2 8/2004 Cmkovich et al.
6,780,156 B2 8/2004 Haueter et al.
6,790,198 B1 9/2004 White et al.
6,792,470 B2 9/2004 Hakenberg et al.
6,796,956 B2 9/2004 Hartlaub et al.
6,799,149 B2 9/2004 Hartlaub
6,809,653 B1 10/2004 Mann et al.
6,811,534 B2 11/2004 Bowman, IV et al.
6,816,605 B2 11/2004 Rowe et al.
6,839,753 B2 1/2005 Biondi et al.
6,852,104 B2 2/2005 Blomquist
6,859,134 B1 2/2005 Heiman et al.
6,871,211 B2 3/2005 Labounty et al.
6,873,268 B2 3/2005 Lebel et al.
6,876,303 B2 4/2005 Reeder et al.
6,885,881 B2 4/2005 Leonhardt
6,891,525 B2 5/2005 Ogoro
6,892,278 B2 5/2005 Ebergen
6,899,695 B2 5/2005 Herrera
6,915,170 B2 7/2005 Engleson et al.
6,923,763 B1 8/2005 Kovatchev et al.
6,924,781 B1 8/2005 Gelbman
6,928,338 B1 8/2005 Buchser et al.
6,928,490 B1 8/2005 Bucholz et al.
6,936,029 B2 8/2005 Mann et al.
6,945,954 B2 9/2005 Hochman et al.
6,948,492 B2 9/2005 Wemeling et al.
6,958,677 B1 10/2005 Carter
6,958,691 B1 10/2005 Anderson et al.
6,958,705 B2 10/2005 Lebel et al.
6,961,448 B2 11/2005 Nichols et al.
6,969,352 B2 11/2005 Chiang et al.
6,969,865 B2 11/2005 Duchon et al.
6,974,437 B2 12/2005 Lebel et al.
6,979,326 B2 12/2005 Mann et al.
6,980,958 B1 12/2005 Surwit et al.
6,985,870 B2 1/2006 Martucci et al.
6,986,347 B2 1/2006 Hickle
6,997,880 B2 2/2006 Carlebach et al.
6,997,920 B2 2/2006 Mann et al.
6,998,984 B1 2/2006 Zittrain
7,016,752 B1 3/2006 Ruben et al.
7,017,293 B2 3/2006 Riley
7,025,743 B2 4/2006 Mann et al.
7,029,455 B2 4/2006 Flaherty
7,038,584 B2 5/2006 Carter
7,060,031 B2 6/2006 Webb et al.
7,060,059 B2 6/2006 Keith et al.
7,069,552 B2 6/2006 Lindberg et al.
7,072,725 B2 7/2006 Bristol et al.
7,079,035 B2 7/2006 Bock et al.
7,092,943 B2 8/2006 Roese et al.
7,096,072 B2 8/2006 Engleson et al.
7,099,809 B2 8/2006 Dori
7,103,419 B2 9/2006 Engleson et al.
7,103,578 B2 9/2006 Beck et al.
7,107,106 B2 9/2006 Engleson et al.
7,108,680 B2 9/2006 Rohr et al.
7,109,878 B2 9/2006 Mann et al.
7,114,002 B1 9/2006 Okumura et al.
7,117,041 B2 10/2006 Engleson et al.
7,136,645 B2 11/2006 Hanson et al.
7,137,964 B2 11/2006 Flaherty
7,142,190 B2 11/2006 Martinez
7,150,741 B2 12/2006 Erickson et al.
7,153,289 B2 12/2006 Vasko
7,154,397 B2 12/2006 Zerhusen et al.
7,156,807 B2 1/2007 Carter et al.
7,158,030 B2 1/2007 Chung
7,161,484 B2 1/2007 Tsoukalis et al.
7,167,755 B2 1/2007 Seeberger et al.
7,167,920 B2 1/2007 Traversat
7,171,277 B2 1/2007 Engleson et al.
7,171,492 B1 1/2007 Borella et al.
7,181,493 B2 2/2007 English et al.
7,185,288 B2 2/2007 McKeever
7,193,514 B2 3/2007 Ritson
7,197,025 B2 3/2007 Chuah
7,201,734 B2 4/2007 Hickle
7,204,823 B2 4/2007 Estes et al.
7,213,009 B2 5/2007 Pestotnik
7,216,802 B1 5/2007 de la Huerga
7,220,240 B2 5/2007 Struys et al.
7,224,979 B2 5/2007 Singhal et al.
7,229,430 B2 6/2007 Hickle et al.

(56) References Cited

U.S. PATENT DOCUMENTS 7,230,529 B2 6/2007 Ketcherside
7,236,936 B2 6/2007 White et al.
7,238,164 B2 7/2007 Childers et al.
7,247,154 B2 7/2007 Hickle
7,248,239 B2 7/2007 Dowling
7,250,856 B2 7/2007 Havekost et al.
7,255,683 B2 8/2007 Vanderveen et al.
7,256,888 B2 8/2007 Staehr et al.
7,258,534 B2 8/2007 Fathallah et al.
7,263,213 B2 8/2007 Rowe
7,267,664 B2 9/2007 Rizzo
7,267,665 B2 9/2007 Steil et al.
7,275,156 B2 9/2007 Balfanz et al.
7,278,983 B2 10/2007 Ireland et al.
7,289,815 B2 10/2007 Gfeller et al.
7,289,948 B1 10/2007 Mohri
7,293,107 B1 11/2007 Hanson et al.
7,295,119 B2 11/2007 Rappaport et al.
7,295,556 B2 11/2007 Roese et al.
7,301,451 B2 11/2007 Hastings
7,308,300 B2 12/2007 Toews et al.
7,315,825 B2 1/2008 Rosenfeld et al.
7,319,386 B2 1/2008 Collins, Jr. et al.
7,324,000 B2 1/2008 Zittrain et al.
7,327,705 B2 2/2008 Fletcher et al.
7,343,224 B2 3/2008 DiGianfilippo et al.
7,346,025 B2 3/2008 Bryson
7,347,836 B2 3/2008 Peterson et al.
7,354,420 B2 4/2008 Steil et al.
7,369,897 B2 5/2008 Boveja et al.
7,369,948 B1 5/2008 Ferenczi et al.
7,383,088 B2 6/2008 Spinelli et al.
7,384,410 B2 6/2008 Eggers et al.
7,398,183 B2 7/2008 Holland et al.
7,398,279 B2 7/2008 Muno, Jr. et al.
7,399,277 B2 7/2008 Saidara et al.
7,402,153 B2 7/2008 Steil et al.
7,420,472 B2 9/2008 Tran
7,432,807 B2 10/2008 Schmitt
7,436,454 B2 10/2008 Yamaguchi et al.
7,447,643 B1 11/2008 Olson
7,454,314 B2 11/2008 Holland et al.
7,457,804 B2 11/2008 Uber, III et al.
7,464,040 B2 12/2008 Joao
7,469,213 B1 12/2008 Rao
7,471,994 B2 12/2008 Ford et al.
7,483,756 B2 1/2009 Engleson et al.
7,489,808 B2 2/2009 Gerder
7,490,021 B2 2/2009 Holland et al.
7,490,048 B2 2/2009 Joao
7,491,187 B2 2/2009 Van Den Berghe et al.
7,519,905 B2 4/2009 Kougiouris et al.
7,523,401 B1 4/2009 Aldridge
7,524,304 B2 4/2009 Genosar
7,551,078 B2 6/2009 Carlson
7,559,321 B2 7/2009 Wermeling et al.
7,565,197 B2 7/2009 Haulbrich et al.
7,572,230 B2 8/2009 Neumann et al.
7,578,802 B2 8/2009 Hickle
7,621,009 B2 11/2009 Elhabashy
D606,533 S 12/2009 De Jong et al.
7,636,718 B1 12/2009 Steen et al.
7,640,172 B2 12/2009 Kuth
7,645,258 B2 1/2010 White et al.
7,647,237 B2 1/2010 Malave et al.
7,662,124 B2 2/2010 Duchon et al.
7,668,731 B2 2/2010 Martucci et al.
7,671,733 B2 3/2010 McNeal et al.
7,678,071 B2 3/2010 Lebel et al.
7,687,678 B2 3/2010 Jacobs
7,697,994 B2 4/2010 VanDanacker et al.
7,698,239 B2 4/2010 Lieuallen
7,705,727 B2 4/2010 Pestotnik
7,724,147 B2 5/2010 Brown et al.
7,739,126 B1 6/2010 Cave
7,746,218 B2 6/2010 Collins, Jr.
7,766,873 B2 8/2010 Moberg et al.
7,776,029 B2 8/2010 Whitehurst et al.
7,776,031 B2 8/2010 Hartlaub et al.
7,785,313 B2 8/2010 Mastrototaro
7,788,369 B2 8/2010 McAllen et al.
7,806,852 B1 10/2010 Jurson
7,806,886 B2 10/2010 Kanderian, Jr. et al.
7,826,981 B2 11/2010 Goode, Jr. et al.
7,835,927 B2 11/2010 Schlotterbeck et al.
7,836,314 B2 11/2010 Chieu
7,856,276 B2 12/2010 Ripart et al.
7,860,583 B2 12/2010 Condurso et al.
7,864,771 B2 1/2011 Tavares et al.
7,868,754 B2 1/2011 Salvat, Jr.
7,871,394 B2 1/2011 Halbert et al.
7,886,231 B2 2/2011 Hopermann et al.
7,895,053 B2 2/2011 Holland et al.
7,896,842 B2 3/2011 Palmroos et al.
7,899,546 B2 3/2011 Sieracki et al.
7,905,710 B2 3/2011 Wang et al.
7,920,061 B2 4/2011 Klein et al.
7,933,780 B2 4/2011 de la Huerga
7,938,796 B2 5/2011 Moubayed
7,945,452 B2 5/2011 Fathallah et al.
7,974,714 B2 7/2011 Hoffberg
7,976,508 B2 7/2011 Hoag
7,996,241 B2 8/2011 Zak
8,034,026 B2 10/2011 Grant
8,038,593 B2 10/2011 Friedman et al.
8,048,040 B2 11/2011 Kiani
8,060,576 B2 11/2011 Chan et al.
8,065,161 B2 11/2011 Howard et al.
8,066,672 B2 11/2011 Mandro
8,075,514 B2 12/2011 Butterfield et al.
8,078,983 B2 12/2011 Davis et al.
8,082,018 B2 12/2011 Duchon et al.
8,082,312 B2 12/2011 Chan et al.
8,095,692 B2 1/2012 Mehta et al.
8,126,730 B2 2/2012 Dicks et al.
8,147,448 B2 4/2012 Sundar et al.
8,149,131 B2 4/2012 Blomquist
8,169,914 B2 5/2012 Bajpai
8,171,094 B2 5/2012 Chan et al.
8,172,798 B2 5/2012 Hungerford et al.
8,185,322 B2 5/2012 Schroeder et al.
8,195,478 B2 6/2012 Petersen et al.
8,206,350 B2 6/2012 Mann et al.
8,219,413 B2 7/2012 Martinez et al.
8,231,578 B2 7/2012 Fathallah et al.
8,234,128 B2 7/2012 Martucci et al.
8,267,892 B2 9/2012 Spencer et al.
8,271,106 B2 9/2012 Wehba et al.
8,287,495 B2 10/2012 Michaud et al.
8,291,337 B2 10/2012 Gannin et al.
8,298,184 B2 10/2012 DiPerna et al.
8,312,272 B1 11/2012 Serenyl et al.
8,352,290 B2 1/2013 Bartz et al.
8,359,338 B2 1/2013 Butterfield et al.
8,380,536 B2 2/2013 Howard et al.
8,387,112 B1 2/2013 Ranjan et al.
8,394,077 B2 3/2013 Jacobson et al.
8,398,592 B2 3/2013 Leibner-Druska
8,403,908 B2 3/2013 Jacobson et al.
8,435,206 B2 5/2013 Evans et al.
8,449,523 B2 5/2013 Brukalo et al.
8,452,953 B2 5/2013 Buck et al.
8,453,645 B2 6/2013 Figueiredo et al.
8,472,630 B2 6/2013 Konrad et al.
8,480,648 B2 7/2013 Burnett et al.
8,486,019 B2 7/2013 White et al.
8,489,427 B2 7/2013 Simpson et al.
8,494,879 B2 7/2013 Davis et al.
8,504,179 B2 8/2013 Blomquist
8,517,990 B2 8/2013 Teel et al.
8,518,021 B2 8/2013 Stewart et al.
8,543,416 B2 9/2013 Palmroos et al.
8,551,038 B2 10/2013 Tsoukalis et al.
8,560,345 B2 10/2013 Wehba et al.

(56) References Cited

U.S. PATENT DOCUMENTS 8,567,681 B2 10/2013 Borges et al.
8,577,692 B2 11/2013 Silkaitis et al.
8,579,884 B2 11/2013 Lanier et al.
8,626,530 B1 1/2014 Tran et al.
8,655,676 B2 2/2014 Wehba et al.
8,660,860 B2 2/2014 Wehba et al.
8,662,388 B2 3/2014 Belkin
8,666,769 B2 3/2014 Butler et al.
8,667,293 B2 3/2014 Birtwhistle et al.
8,687,811 B2 4/2014 Nierzwick et al.
8,700,421 B2 4/2014 Feng et al.
8,731,960 B2 5/2014 Butler et al.
8,768,719 B2 7/2014 Wehba et al.
8,771,251 B2 7/2014 Ruchti et al.
8,777,894 B2 7/2014 Butterfield et al.
8,777,895 B2 7/2014 Hsu et al.
8,799,012 B2 8/2014 Butler et al.
8,876,793 B2 11/2014 Ledford et al.
8,886,316 B1 11/2014 Juels
8,922,330 B2 12/2014 Moberg et al.
8,936,565 B2 1/2015 Chawla
8,945,043 B2 2/2015 Lee et al.
8,952,794 B2 2/2015 Blomquist et al.
8,959,617 B2 2/2015 Newlin et al.
8,998,100 B2 4/2015 Halbert et al.
9,026,370 B2 5/2015 Rubalcaba et al.
9,069,887 B2 6/2015 Gupta et al.
9,077,544 B2 7/2015 Baker et al.
9,089,642 B2 7/2015 Murphy et al.
9,114,217 B2 8/2015 Sur et al.
9,123,077 B2 9/2015 Silkaitis et al.
9,192,712 B2 11/2015 DeBelser et al.
9,240,002 B2 1/2016 Hume et al.
9,283,339 B2 3/2016 Sherman
9,292,692 B2 3/2016 Wallrabenstein
9,302,035 B2 4/2016 Marseille et al.
9,313,154 B1 4/2016 Son
9,381,296 B2 7/2016 Arrizza et al.
9,393,362 B2 7/2016 Cozmi et al.
9,430,655 B1 8/2016 Stockton et al.
9,438,580 B2 9/2016 Kupper
9,483,615 B2 11/2016 Roberts
9,498,583 B2 11/2016 Sur et al.
9,539,383 B2 1/2017 Kohlbrecher
9,572,923 B2 2/2017 Howard et al.
9,594,875 B2 3/2017 Arrizza et al.
9,604,000 B2 3/2017 Wehba et al.
9,641,432 B2 5/2017 Jha et al.
9,649,431 B2 5/2017 Gray et al.
9,662,436 B2 5/2017 Belkin et al.
9,690,909 B2 6/2017 Stewart et al.
9,707,341 B2 7/2017 Dumas, III et al.
9,717,845 B2 8/2017 Istoc
9,724,470 B2 8/2017 Day et al.
9,729,330 B2 8/2017 Verma
9,764,082 B2 9/2017 Day et al.
9,886,550 B2 2/2018 Lee et al.
9,943,269 B2 4/2018 Muhsin et al.
9,967,739 B2 5/2018 Proennecke et al.
9,971,871 B2 5/2018 Arrizza et al.
9,980,140 B1 5/2018 Spencer et al.
9,995,611 B2 6/2018 Ruchti et al.
10,022,498 B2 7/2018 Ruchti et al.
10,042,986 B2 8/2018 Ruchti et al.
10,046,112 B2 8/2018 Oruklu et al.
10,166,328 B2 1/2019 Oruklu et al.
10,173,008 B2 1/2019 Simpson et al.
10,188,849 B2 1/2019 Fangrow
10,233,179 B2 3/2019 Ng et al.
10,238,799 B2 3/2019 Kohlbrecher
10,238,801 B2 3/2019 Wehba et al.
10,242,060 B2 3/2019 Butler et al.
10,300,194 B2 5/2019 Day et al.
10,311,972 B2 * 6/2019 Kohlbrecher ....... G06F 11/3006
10,314,974 B2 6/2019 Day et al.
10,333,843 B2 6/2019 Jha et al.
10,341,866 B1 7/2019 Spencer et al.
10,356,087 B1 7/2019 Vetter
10,409,995 B1 9/2019 Wasiq
10,430,761 B2 10/2019 Hume et al.
10,434,246 B2 10/2019 Silkaitis et al.
10,438,001 B1 10/2019 Hariprasad
10,452,842 B2 10/2019 Dhondse
10,453,157 B2 10/2019 Kamen et al.
10,463,788 B2 11/2019 Day
10,516,536 B2 12/2019 Rommel
10,617,815 B2 4/2020 Day et al.
10,646,651 B2 5/2020 Day et al.
10,681,207 B1 6/2020 Johnson et al.
10,692,595 B2 6/2020 Xavier et al.
10,728,262 B1 7/2020 Vaswani
10,740,436 B2 8/2020 Moskal et al.
10,741,280 B2 8/2020 Xavier et al.
10,757,219 B2 8/2020 Moskal
10,765,799 B2 9/2020 Belkin et al.
10,799,632 B2 10/2020 Kohlbrecher
10,812,380 B2 10/2020 Jha et al.
10,861,592 B2 12/2020 Xavier et al.
10,898,641 B2 1/2021 Day et al.
10,950,339 B2 3/2021 Xavier et al.
10,964,428 B2 3/2021 Xavier et al.
11,013,861 B2 5/2021 Wehba et al.
11,037,668 B2 6/2021 Ruchti et al.
11,052,193 B2 7/2021 Day et al.
11,139,058 B2 10/2021 Xavier et al.
11,151,290 B2 10/2021 Karakoyunlu et al.
11,152,108 B2 10/2021 Xavier et al.
11,152,109 B2 10/2021 Xavier et al.
11,152,110 B2 10/2021 Xavier et al.
11,194,810 B2 12/2021 Butler et al.
11,235,100 B2 2/2022 Howard et al.
11,289,183 B2 3/2022 Kohlbrecher
11,309,070 B2 4/2022 Xavier et al.
11,324,960 B2 5/2022 Sjoquist
11,328,804 B2 5/2022 Xavier et al.
11,328,805 B2 5/2022 Xavier et al.
11,373,753 B2 6/2022 Xavier et al.
11,437,132 B2 9/2022 Xavier et al.
11,470,000 B2 10/2022 Jha et al.
11,483,402 B2 10/2022 Xavier et al.
11,483,403 B2 10/2022 Xavier et al.
11,501,877 B2 * 11/2022 Kohlbrecher ....... G06F 11/3409
11,571,508 B2 2/2023 Jacobson et al.
11,574,721 B2 2/2023 Kohlbrecher
11,574,737 B2 2/2023 Dharwad et al.
11,587,669 B2 2/2023 Xavier et al.
11,590,057 B2 2/2023 Tagliamento et al.
11,594,326 B2 2/2023 Xavier et al.
11,605,468 B2 3/2023 Jacobson et al.
11,626,205 B2 4/2023 Arrizza et al.
11,628,246 B2 4/2023 Day et al.
11,628,254 B2 4/2023 Day et al.
11,654,237 B2 5/2023 Wehba et al.
11,670,416 B2 6/2023 Xavier et al.
11,763,927 B2 9/2023 Ruchti et al.
11,783,935 B2 10/2023 Xavier et al.
11,881,297 B2 1/2024 Xavier et al.
11,923,076 B2 3/2024 Xavier et al.
11,986,623 B2 5/2024 Jacobson et al.
11,996,188 B2 5/2024 Arrizza et al.
12,002,562 B2 6/2024 Kohlbrecher
12,036,390 B2 7/2024 Wehba et al.
12,040,068 B2 7/2024 Xavier et al.
12,042,623 B2 7/2024 Day et al.
12,042,631 B2 7/2024 Day et al.
12,046,361 B2 7/2024 Xavier et al.
12,047,292 B2 7/2024 Jha et al.
12,097,351 B2 9/2024 Belkin et al.
12,130,910 B2 10/2024 Vivek et al.
12,142,370 B2 11/2024 Xavier et al.
12,205,702 B2 1/2025 Xavier et al.
12,303,464 B2 5/2025 Tagliamento et al.
12,337,142 B2 6/2025 Wehba et al.
12,380,982 B2 8/2025 Kohlbrecher

(56) References Cited

U.S. PATENT DOCUMENTS 12,380,997 B2 8/2025 Arrizza et al.
12,395,429 B2 8/2025 Jha et al.
12,420,009 B2 9/2025 Day et al.
12,592,305 B2 3/2026 Xavier et al.
2001/0016056 A1 8/2001 Westphal et al.
2001/0029178 A1 10/2001 Criss et al.
2001/0031944 A1 10/2001 Peterson et al.
2001/0032099 A1 10/2001 Joao
2001/0037060 A1 11/2001 Thompson et al.
2001/0044731 A1 11/2001 Coffman et al.
2001/0048027 A1 12/2001 Walsh
2001/0051787 A1 12/2001 Haller et al.
2001/0056358 A1 12/2001 Dulong et al.
2002/0010595 A1 1/2002 Kapp
2002/0013551 A1 1/2002 Zaitsu et al.
2002/0013723 A1 1/2002 Mise
2002/0015018 A1 2/2002 Shimazu et al.
2002/0019584 A1 2/2002 Schulze et al.
2002/0021700 A1 2/2002 Hata et al.
2002/0026103 A1 2/2002 Norris et al.
2002/0029776 A1 3/2002 Blomquist
2002/0032583 A1 3/2002 Joao
2002/0040208 A1 4/2002 Flaherty et al.
2002/0040282 A1 4/2002 Bailey et al.
2002/0044043 A1 4/2002 Chaco et al.
2002/0044059 A1 4/2002 Reeder et al.
2002/0046335 A1 4/2002 Baum-Waidner
2002/0077852 A1 6/2002 Ford et al.
2002/0082728 A1 6/2002 Mueller et al.
2002/0087115 A1 7/2002 Hartlaub
2002/0087116 A1 7/2002 Hartlaub
2002/0095486 A1 7/2002 Bahl
2002/0103675 A1 8/2002 Vanelli
2002/0123905 A1 9/2002 Goodroe et al.
2002/0143580 A1 10/2002 Bristol et al.
2002/0152239 A1 10/2002 Bautista-Lloyd et al.
2002/0154600 A1 10/2002 Ido et al.
2002/0161591 A1 10/2002 Danneels
2002/0169636 A1 11/2002 Eggers et al.
2002/0173702 A1 11/2002 Lebel et al.
2002/0173875 A1 11/2002 Wallace et al.
2002/0193679 A1 12/2002 Malave et al.
2002/0194329 A1 12/2002 Alling
2003/0009244 A1 1/2003 Engleson
2003/0013959 A1 1/2003 Grunwald et al.
2003/0014222 A1 1/2003 Klass et al.
2003/0014817 A1 1/2003 Gallant et al.
2003/0025602 A1 2/2003 Medema et al.
2003/0028082 A1 2/2003 Thompson
2003/0036683 A1 2/2003 Kehr et al.
2003/0036744 A1 2/2003 Struys et al.
2003/0047126 A1 3/2003 Tomaschko
2003/0047600 A1 3/2003 Nakanishi et al.
2003/0050621 A1 3/2003 Lebel et al.
2003/0059750 A1 3/2003 Bindler et al.
2003/0060688 A1 3/2003 Ciarniello et al.
2003/0069963 A1 4/2003 Jayant et al.
2003/0079746 A1 5/2003 Hickle
2003/0097529 A1 5/2003 Arimilli et al.
2003/0104982 A1 6/2003 Wittmann et al.
2003/0105389 A1 6/2003 Noonan et al.
2003/0106553 A1 6/2003 Vanderveen
2003/0114836 A1 6/2003 Estes et al.
2003/0115358 A1 6/2003 Yun
2003/0120384 A1 6/2003 Haitin et al.
2003/0125662 A1 7/2003 Bui
2003/0130616 A1 7/2003 Steil
2003/0135087 A1 7/2003 Hickle et al.
2003/0139701 A1 7/2003 White et al.
2003/0140928 A1 7/2003 Bui et al.
2003/0140929 A1 7/2003 Wilkes et al.
2003/0141981 A1 7/2003 Bui et al.
2003/0143746 A1 7/2003 Sage, Jr.
2003/0144878 A1 7/2003 Wilkes et al.
2003/0158749 A1 8/2003 Olchanski et al.
2003/0187338 A1 10/2003 Say et al.
2003/0200116 A1 10/2003 Forrester
2003/0204416 A1 10/2003 Acharya
2003/0204781 A1 10/2003 Peebles et al.
2003/0212364 A1 11/2003 Mann et al.
2003/0212379 A1 11/2003 Bylund et al.
2003/0212821 A1 11/2003 Gillies et al.
2003/0216831 A1 11/2003 Hart et al.
2003/0217962 A1 11/2003 Childers et al.
2004/0008123 A1 1/2004 Carrender et al.
2004/0010786 A1 1/2004 Cool et al.
2004/0015132 A1 1/2004 Brown
2004/0019464 A1 1/2004 Martucci et al.
2004/0019607 A1 1/2004 Moubayed et al.
2004/0030323 A1 2/2004 Ullestad et al.
2004/0039257 A1 2/2004 Hickle
2004/0057226 A1 3/2004 Berthou et al.
2004/0064341 A1 4/2004 Langan et al.
2004/0064342 A1 4/2004 Browne et al.
2004/0064435 A1 4/2004 Moubayed et al.
2004/0073161 A1 4/2004 Tachibana
2004/0073811 A1 4/2004 Sanin
2004/0077934 A1 4/2004 Massad
2004/0078231 A1 4/2004 Wilkes et al.
2004/0078236 A1 4/2004 Stoodley et al.
2004/0085186 A1 5/2004 Eveland et al.
2004/0104271 A1 6/2004 Martucci et al.
2004/0122530 A1 6/2004 Hansen
2004/0128162 A1 7/2004 Schlotterbeck et al.
2004/0128163 A1 7/2004 Goodman et al.
2004/0133441 A1 7/2004 Brady et al.
2004/0139004 A1 7/2004 Cohen et al.
2004/0145480 A1 7/2004 Despotis
2004/0147034 A1 7/2004 Gore et al.
2004/0167464 A1 8/2004 Ireland et al.
2004/0167465 A1 8/2004 Kohler
2004/0167804 A1 8/2004 Simpson
2004/0172222 A1 9/2004 Simpson et al.
2004/0172283 A1 9/2004 Vanderveen
2004/0172301 A1 9/2004 Mihai et al.
2004/0172302 A1 9/2004 Martucci et al.
2004/0176667 A1 9/2004 Mihai et al.
2004/0176980 A1 9/2004 Bulitta et al.
2004/0176984 A1 9/2004 White et al.
2004/0181314 A1* 9/2004 Zaleski ............... A61M 16/021 700/282
2004/0189708 A1 9/2004 Larcheveque et al.
2004/0193325 A1 9/2004 Bonderud
2004/0193328 A1 9/2004 Butterfield et al.
2004/0193453 A1 9/2004 Butterfield et al.
2004/0204673 A1 10/2004 Flaherty et al.
2004/0215278 A1 10/2004 Stegink et al.
2004/0220517 A1 11/2004 Starkweather et al.
2004/0225252 A1 11/2004 Gillespie et al.
2004/0236240 A1 11/2004 Kraus et al.
2004/0243438 A1 12/2004 Mintz
2004/0254434 A1 12/2004 Goodnow et al.
2005/0010269 A1 1/2005 Lebel et al.
2005/0020886 A1 1/2005 Hutchinson et al.
2005/0021006 A1 1/2005 Tonnies
2005/0027560 A1 2/2005 Cook
2005/0027567 A1 2/2005 Taha
2005/0038311 A1 2/2005 Kuth
2005/0038669 A1 2/2005 Sachdeva et al.
2005/0038680 A1 2/2005 McMahon
2005/0040226 A1 2/2005 Al-Sheikh
2005/0043620 A1 2/2005 Fallows et al.
2005/0049910 A1 3/2005 Lancaster et al.
2005/0055242 A1 3/2005 Bello et al.
2005/0055244 A1 3/2005 Mullan et al.
2005/0065465 A1 3/2005 Lebel et al.
2005/0065817 A1 3/2005 Mihai et al.
2005/0075544 A1 4/2005 Shapiro et al.
2005/0080801 A1 4/2005 Kothandaraman et al.
2005/0086071 A1 4/2005 Fox, Jr. et al.
2005/0086072 A1 4/2005 Fox
2005/0088704 A1 4/2005 Vaschillo et al.
2005/0090808 A1 4/2005 Malave et al.
2005/0099624 A1 5/2005 Staehr

(56) References Cited

U.S. PATENT DOCUMENTS

2005/0102162 A1 5/2005 Blumenfeld
2005/0102165 A1 5/2005 Oshita et al.
2005/0102167 A1 5/2005 Kapoor
2005/0102669 A1 5/2005 Marney et al.
2005/0107923 A1 5/2005 Vanderveen
2005/0108057 A1 5/2005 Cohen et al.
2005/0117529 A1 6/2005 Ramos-Escano
2005/0119788 A1 6/2005 Engleson et al.
2005/0119914 A1 6/2005 Batch
2005/0131739 A1 6/2005 Rabinowitz et al.
2005/0135306 A1 6/2005 McAllen et al.
2005/0137522 A1 6/2005 Aoki
2005/0137573 A1 6/2005 McLaughlin
2005/0137653 A1 6/2005 Friedman et al.
2005/0138428 A1 6/2005 McAllen et al.
2005/0154769 A1 7/2005 Eckart et al.
2005/0160057 A1 7/2005 Wefers et al.
2005/0171503 A1 8/2005 Van Den Berghe et al.
2005/0171815 A1 8/2005 Vanderveen
2005/0177096 A1 8/2005 Bollish et al.
2005/0177395 A1 8/2005 Blomquist
2005/0182306 A1 8/2005 Sloan
2005/0182355 A1 8/2005 Bui
2005/0187950 A1 8/2005 Parker
2005/0192557 A1 9/2005 Brauker et al.
2005/0197554 A1 9/2005 Polcha
2005/0197621 A1 9/2005 Poulsen et al.
2005/0210037 A1 9/2005 Wefers et al.
2005/0216479 A1 9/2005 Wefers et al.
2005/0216480 A1 9/2005 Wefers et al.
2005/0223045 A1 10/2005 Funahashi et al.
2005/0224083 A1 10/2005 Crass
2005/0234746 A1 10/2005 Funahashi
2005/0240305 A1 10/2005 Bogash et al.
2005/0246416 A1 11/2005 Blomquist
2005/0251418 A1 11/2005 Fox, Jr. et al.
2005/0261660 A1 11/2005 Choi
2005/0273059 A1 12/2005 Mernoe et al.
2005/0273367 A1 12/2005 Nourie et al.
2005/0277873 A1 12/2005 Stewart et al.
2005/0277890 A1 12/2005 Stewart et al.
2005/0277911 A1 12/2005 Stewart et al.
2005/0278194 A1 12/2005 Holland et al.
2006/0002556 A1 1/2006 Paul
2006/0004772 A1 1/2006 Hagan et al.
2006/0009727 A1 1/2006 O'Mahony et al.
2006/0009734 A1 1/2006 Martin
2006/0010098 A1 1/2006 Goodnow et al.
2006/0042139 A1 3/2006 Mendes
2006/0047270 A1 3/2006 Shelton
2006/0053036 A1 3/2006 Coffman et al.
2006/0064020 A1 3/2006 Burnes et al.
2006/0074633 A1 4/2006 Mahesh et al.
2006/0074920 A1 4/2006 Wefers et al.
2006/0079831 A1 4/2006 Gilbert
2006/0089539 A1 4/2006 Miodownik et al.
2006/0089854 A1 4/2006 Holland et al.
2006/0089855 A1 4/2006 Holland et al.
2006/0100746 A1 5/2006 Leibner-Druska
2006/0100907 A1 5/2006 Holland et al.
2006/0106649 A1 5/2006 Eggers et al.
2006/0111943 A1 5/2006 Wu
2006/0116639 A1 6/2006 Russell
2006/0116904 A1 6/2006 Brem
2006/0116907 A1 6/2006 Rhodes et al.
2006/0122481 A1 6/2006 Sievenpiper et al.
2006/0122867 A1 6/2006 Eggers et al.
2006/0129140 A1 6/2006 Todd et al.
2006/0129429 A1 6/2006 Moubayed et al.
2006/0129434 A1 6/2006 Smitherman et al.
2006/0129435 A1 6/2006 Smitherman et al.
2006/0136266 A1 6/2006 Tarassenko et al.
2006/0136271 A1 6/2006 Eggers et al.
2006/0143051 A1 6/2006 Eggers et al.
2006/0173260 A1 8/2006 Gaoni et al.
2006/0173406 A1 8/2006 Hayes et al.
2006/0173715 A1 8/2006 Wang et al.
2006/0173927 A1 8/2006 Beyer et al.
2006/0190302 A1 8/2006 Eggers et al.
2006/0195022 A1 8/2006 Trepagnier et al.
2006/0200007 A1 9/2006 Brockway et al.
2006/0200369 A1 9/2006 Batch et al.
2006/0211404 A1 9/2006 Cromp et al.
2006/0224141 A1 10/2006 Rush et al.
2006/0229551 A1 10/2006 Martinez et al.
2006/0229557 A1 10/2006 Fathallah et al.
2006/0229918 A1 10/2006 Fotsch et al.
2006/0236373 A1 10/2006 Graves et al.
2006/0247606 A1 11/2006 Batch
2006/0253554 A1 11/2006 Uwais
2006/0258985 A1 11/2006 Russell
2006/0259327 A1 11/2006 Hoag
2006/0264895 A1 11/2006 Flanders
2006/0265186 A1 11/2006 Holland et al.
2006/0265246 A1 11/2006 Hoag
2006/0267753 A1 11/2006 Hussey et al.
2006/0268710 A1 11/2006 Appanna et al.
2006/0270971 A1 11/2006 Gelfand et al.
2006/0277206 A1 12/2006 Bailey et al.
2006/0287885 A1 12/2006 Frick
2007/0015972 A1 1/2007 Wang et al.
2007/0016443 A1 1/2007 Wachman et al.
2007/0021715 A1 1/2007 Kohlbrenner et al.
2007/0027506 A1 2/2007 Stender et al.
2007/0060796 A1 3/2007 Kim
2007/0060870 A1 3/2007 Tolle et al.
2007/0060871 A1 3/2007 Istoc
2007/0061393 A1 3/2007 Moore
2007/0065363 A1 3/2007 Dalal et al.
2007/0073419 A1 3/2007 Sesay
2007/0073822 A1 3/2007 Bennett et al.
2007/0078314 A1 4/2007 Grounsell
2007/0083870 A1 4/2007 Kanakogi
2007/0088333 A1 4/2007 Levin et al.
2007/0093786 A1 4/2007 Goldsmith et al.
2007/0100665 A1 5/2007 Brown
2007/0100667 A1 5/2007 Bardy
2007/0106126 A1 5/2007 Mannheimer et al.
2007/0112298 A1 5/2007 Mueller et al.
2007/0116037 A1 5/2007 Moore
2007/0118405 A1 5/2007 Campbell et al.
2007/0135866 A1 6/2007 Baker et al.
2007/0136098 A1 6/2007 Smythe et al.
2007/0142822 A1 6/2007 Remde
2007/0156282 A1 7/2007 Dunn
2007/0156452 A1 7/2007 Batch
2007/0169008 A1 7/2007 Varanasi et al.
2007/0179448 A1 8/2007 Lim et al.
2007/0186923 A1 8/2007 Poutiatine et al.
2007/0191817 A1 8/2007 Martin
2007/0191973 A1 8/2007 Holzbauer et al.
2007/0213657 A1 9/2007 Jennewine et al.
2007/0213684 A1 9/2007 Hickle et al.
2007/0214003 A1 9/2007 Holland et al.
2007/0215545 A1 9/2007 Bissler et al.
2007/0229249 A1 10/2007 McNeal et al.
2007/0232867 A1 10/2007 Hansmann
2007/0233035 A1 10/2007 Wehba et al.
2007/0233049 A1 10/2007 Wehba et al.
2007/0233206 A1 10/2007 Frikart
2007/0233520 A1 10/2007 Wehba et al.
2007/0240215 A1 10/2007 Flores
2007/0251835 A1 11/2007 Mehta et al.
2007/0253021 A1 11/2007 Mehta et al.
2007/0254593 A1 11/2007 Jollota et al.
2007/0255125 A1* 11/2007 Moberg ................ G16H 20/17
600/365
2007/0257788 A1 11/2007 Carlson
2007/0258395 A1 11/2007 Jollota et al.
2007/0288423 A1 12/2007 Kimoto
2007/0291647 A1 12/2007 Smith
2007/0299687 A1 12/2007 Palmer et al.
2007/0299695 A1 12/2007 Jung et al.
2008/0001771 A1 1/2008 Faoro et al.

(56) References Cited

U.S. PATENT DOCUMENTS

2008/0004904 A1 1/2008 Tran
2008/0009684 A1 1/2008 Corsetti et al.
2008/0013559 A1 1/2008 Smith
2008/0033361 A1 2/2008 Evans et al.
2008/0033966 A1 2/2008 Wahl
2008/0034323 A1 2/2008 Blomquist
2008/0041942 A1 2/2008 Aissa
2008/0052704 A1 2/2008 Wysocki
2008/0065007 A1 3/2008 Peterson et al.
2008/0065417 A1 3/2008 Jung et al.
2008/0071217 A1 3/2008 Moubayed et al.
2008/0071251 A1 3/2008 Moubayed et al.
2008/0086088 A1 4/2008 Malcolm
2008/0091466 A1 4/2008 Butler et al.
2008/0095339 A1 4/2008 Elliott
2008/0097289 A1 4/2008 Steil et al.
2008/0097552 A1 4/2008 Dicks et al.
2008/0126969 A1 5/2008 Blomquist
2008/0139907 A1 6/2008 Rao et al.
2008/0148047 A1 6/2008 Appenzeller et al.
2008/0149117 A1 6/2008 Raghuram
2008/0154177 A1* 6/2008 Moubayed ............ G16H 20/17 604/500
2008/0172337 A1 7/2008 Banfield et al.
2008/0184219 A1 7/2008 Matsumoto
2008/0188796 A1 8/2008 Steil et al.
2008/0200870 A1 8/2008 Palmroos et al.
2008/0214919 A1 9/2008 Harmon et al.
2008/0243055 A1 10/2008 Fathallah et al.
2008/0244717 A1 10/2008 Jelatis et al.
2008/0246748 A1 10/2008 Cassidy et al.
2008/0256305 A1 10/2008 Kwon
2008/0259926 A1 10/2008 Tavares et al.
2008/0262469 A1 10/2008 Bristol et al.
2008/0269714 A1 10/2008 Mastrototaro et al.
2008/0269723 A1 10/2008 Mastrototaro et al.
2008/0275384 A1 11/2008 Mastrototaro et al.
2008/0300572 A1 12/2008 Rankers et al.
2008/0301298 A1 12/2008 Bernardi et al.
2008/0320387 A1 12/2008 Sasaki et al.
2008/0320466 A1 12/2008 Dias
2009/0003554 A1 1/2009 Katis et al.
2009/0005703 A1 1/2009 Fasciano
2009/0005728 A1 1/2009 Weinert et al.
2009/0006061 A1 1/2009 Thukral et al.
2009/0006129 A1 1/2009 Thukral
2009/0006133 A1 1/2009 Weinert
2009/0018495 A1 1/2009 Panduro
2009/0036750 A1 2/2009 Weinstein et al.
2009/0051560 A1 2/2009 Manning et al.
2009/0054743 A1 2/2009 Stewart
2009/0054754 A1 2/2009 McMahon et al.
2009/0057399 A1 3/2009 Sajkowsky
2009/0063187 A1 3/2009 Johnson et al.
2009/0069785 A1 3/2009 Miller et al.
2009/0088701 A1 4/2009 Larsen
2009/0099866 A1 4/2009 Newman
2009/0099867 A1 4/2009 Newman
2009/0135196 A1 5/2009 Holland et al.
2009/0143662 A1 6/2009 Estes et al.
2009/0149743 A1 6/2009 Barron et al.
2009/0150174 A1 6/2009 Buck et al.
2009/0150439 A1 6/2009 Gejdos et al.
2009/0150878 A1 6/2009 Pathak et al.
2009/0156991 A1 6/2009 Roberts
2009/0157695 A1 6/2009 Roberts
2009/0158274 A1 6/2009 Roberts
2009/0177146 A1 7/2009 Nesbitt et al.
2009/0177769 A1 7/2009 Roberts
2009/0177992 A1 7/2009 Rubalcaba et al.
2009/0183147 A1 7/2009 Davis et al.
2009/0209938 A1 8/2009 Aalto-Setala
2009/0210250 A1 8/2009 Prax et al.
2009/0221890 A1 9/2009 Saffer et al.
2009/0231249 A1 9/2009 Wang et al.
2009/0270833 A1 10/2009 DeBelser
2009/0275886 A1 11/2009 Blomquist et al.
2009/0275896 A1 11/2009 Kamen et al.
2009/0284691 A1 11/2009 Marhefka et al.
2009/0292340 A1 11/2009 Mass et al.
2009/0306573 A1 12/2009 Gagner et al.
2009/0326340 A1 12/2009 Wang
2009/0326516 A1 12/2009 Bangera et al.
2010/0008377 A1 1/2010 Hasti et al.
2010/0022988 A1 1/2010 Wochner
2010/0036310 A1 2/2010 Hillman
2010/0056992 A1 3/2010 Hayter
2010/0083060 A1 4/2010 Rahman
2010/0088507 A1 4/2010 Cho
2010/0095229 A1 4/2010 Dixon et al.
2010/0121170 A1 5/2010 Rule
2010/0121246 A1 5/2010 Peters et al.
2010/0121415 A1 5/2010 Skelton et al.
2010/0121654 A1 5/2010 Portnoy et al.
2010/0121752 A1 5/2010 Banigan et al.
2010/0130933 A1 5/2010 Holland et al.
2010/0131434 A1 5/2010 Magent et al.
2010/0138523 A1 6/2010 Umess et al.
2010/0146137 A1 6/2010 Wu et al.
2010/0156633 A1 6/2010 Buck et al.
2010/0160854 A1 6/2010 Gauthier
2010/0160860 A1 6/2010 Celentano et al.
2010/0174266 A1 7/2010 Estes
2010/0191525 A1 7/2010 Rabenko et al.
2010/0198034 A1 8/2010 Thomas et al.
2010/0198196 A1 8/2010 Wei
2010/0200506 A1 8/2010 Ware et al.
2010/0204574 A1 8/2010 Duchon et al.
2010/0209268 A1 8/2010 Davis
2010/0212675 A1 8/2010 Walling et al.
2010/0217621 A1 8/2010 Schoenberg
2010/0234708 A1 9/2010 Buck et al.
2010/0250732 A1 9/2010 Bucknell
2010/0271479 A1 10/2010 Heydlauf
2010/0273738 A1 10/2010 Valcke et al.
2010/0274218 A1 10/2010 Yodfat et al.
2010/0280486 A1 11/2010 Khair et al.
2010/0292634 A1 11/2010 Kircher
2010/0298765 A1 11/2010 Budiman et al.
2010/0305499 A1 12/2010 Matsiev
2010/0318025 A1 12/2010 John
2011/0001605 A1 1/2011 Kiani et al.
2011/0021898 A1 1/2011 Wei et al.
2011/0028885 A1 2/2011 Eggers et al.
2011/0040158 A1 2/2011 Katz et al.
2011/0060758 A1 3/2011 Schlotterbeck et al.
2011/0067092 A1 3/2011 Baker
2011/0071844 A1 3/2011 Cannon et al.
2011/0072379 A1 3/2011 Gannon
2011/0078253 A1 3/2011 Chan et al.
2011/0078608 A1 3/2011 Gannon et al.
2011/0093284 A1 4/2011 Dicks et al.
2011/0099313 A1 4/2011 Bolanowski
2011/0106318 A1 5/2011 Ledford et al.
2011/0125095 A1 5/2011 Lebel et al.
2011/0133946 A1 6/2011 Kopp
2011/0138185 A1 6/2011 Ju et al.
2011/0166628 A1 7/2011 Jain
2011/0175728 A1 7/2011 Baker, Jr.
2011/0178462 A1* 7/2011 Moberg ................ H04L 63/061 604/151
2011/0185010 A1 7/2011 Shatsky et al.
2011/0196748 A1 8/2011 Caron et al.
2011/0231216 A1 9/2011 Fyke et al.
2011/0252230 A1 10/2011 Segre et al.
2011/0257496 A1 10/2011 Terashima et al.
2011/0257798 A1 10/2011 Ali et al.
2011/0259954 A1 10/2011 Bartz et al.
2011/0264043 A1 10/2011 Kotnick et al.
2011/0264044 A1 10/2011 Bartz et al.
2011/0266221 A1 11/2011 Ware et al.
2011/0270045 A1 11/2011 Lebel et al.
2011/0275904 A1 11/2011 Lebel et al.
2011/0286457 A1 11/2011 Ee

(56) References Cited

U.S. PATENT DOCUMENTS

2011/0289162 A1 11/2011 Furlong
2011/0289314 A1 11/2011 Whitcomb
2011/0289497 A1 11/2011 Kiaie et al.
2011/0295196 A1 12/2011 Chazot et al.
2011/0295341 A1 12/2011 Estes et al.
2011/0296051 A1 12/2011 Vange
2011/0296411 A1 12/2011 Tang et al.
2011/0313789 A1 12/2011 Karmen et al.
2011/0319813 A1 12/2011 Kamen et al.
2011/0320049 A1 12/2011 Chossat et al.
2012/0005680 A1 1/2012 Dolby et al.
2012/0011253 A1* 1/2012 Friedman ................ H04L 41/06 709/224
2012/0016305 A1 1/2012 Jollota
2012/0029941 A1 2/2012 Malave et al.
2012/0036102 A1 2/2012 Fletcher et al.
2012/0036550 A1 2/2012 Rodriguez
2012/0066501 A1 3/2012 Xiong
2012/0070045 A1 3/2012 Vesper et al.
2012/0079084 A1 3/2012 Forssell et al.
2012/0095437 A1 4/2012 Hemmerling
2012/0112903 A1 5/2012 Kaib et al.
2012/0130198 A1 5/2012 Beaule
2012/0130308 A1 5/2012 Silkaitis et al.
2012/0143116 A1 6/2012 Ware et al.
2012/0150556 A1 6/2012 Galasso et al.
2012/0157920 A1 6/2012 Flachbart et al.
2012/0172802 A1 7/2012 Blomquist et al.
2012/0179135 A1 7/2012 Rinehart et al.
2012/0179136 A1 7/2012 Rinehart et al.
2012/0185267 A1 7/2012 Kamen et al.
2012/0203177 A1 8/2012 Lanier
2012/0210123 A1 8/2012 Castelnuovo
2012/0245554 A1 9/2012 Kawamura
2012/0259978 A1* 10/2012 Petersen ............. H04L 43/0852 709/224
2012/0260012 A1 10/2012 Gao-Saari et al.
2012/0277716 A1 11/2012 Ali et al.
2012/0283630 A1 11/2012 Lee et al.
2012/0284734 A1 11/2012 McQuaid et al.
2012/0323212 A1 12/2012 Murphy
2012/0330380 A1 12/2012 Corndorf
2013/0006666 A1 1/2013 Schneider
2013/0006702 A1 1/2013 Wu
2013/0012877 A1 1/2013 Debelser et al.
2013/0012879 A1 1/2013 Debelser et al.
2013/0012880 A1 1/2013 Blomquist
2013/0015980 A1 1/2013 Evans et al.
2013/0036403 A1 2/2013 Geist
2013/0036412 A1 2/2013 Birtwhistle et al.
2013/0047113 A1* 2/2013 Hume .................... G16H 20/17 715/771
2013/0066265 A1 3/2013 Grant
2013/0072872 A1 3/2013 Yodfat et al.
2013/0085689 A1 4/2013 Sur et al.
2013/0091350 A1 4/2013 Gluck
2013/0096444 A1 4/2013 Condurso et al.
2013/0096648 A1 4/2013 Benson
2013/0102963 A1 4/2013 Marsh et al.
2013/0114594 A1 5/2013 Van Zijst
2013/0116578 A1 5/2013 An
2013/0132721 A1 5/2013 Busser
2013/0133083 A1 5/2013 Kurumai
2013/0138452 A1 5/2013 Cork et al.
2013/0144206 A1 6/2013 Lee et al.
2013/0150824 A1 6/2013 Estes et al.
2013/0158504 A1 6/2013 Ruchti et al.
2013/0167245 A1 6/2013 Birtwhistle et al.
2013/0173473 A1 7/2013 Birtwhistle et al.
2013/0191770 A1 7/2013 Bartz et al.
2013/0204188 A1 8/2013 Kamen et al.
2013/0218080 A1 8/2013 Peterfreund et al.
2013/0261993 A1 10/2013 Ruchti et al.
2013/0274669 A1 10/2013 Stempfle et al.
2013/0275539 A1 10/2013 Gross et al.
2013/0276785 A1* 10/2013 Melker ............. A61M 16/0677 128/204.23
2013/0291116 A1 10/2013 Homer
2013/0296823 A1 11/2013 Melker et al.
2013/0296984 A1 11/2013 Burnett et al.
2013/0317753 A1 11/2013 Kamen et al.
2013/0346108 A1 12/2013 Kamen et al.
2014/0025392 A1 1/2014 Chandrasenan
2014/0039446 A1 2/2014 Day
2014/0108783 A1 4/2014 Suzuki
2014/0142540 A1 5/2014 Imhof
2014/0142963 A1 5/2014 Hill et al.
2014/0163517 A1 6/2014 Finan et al.
2014/0172994 A1 6/2014 Raumann et al.
2014/0180711 A1 6/2014 Kamen et al.
2014/0197950 A1 7/2014 Shupp et al.
2014/0215490 A1 7/2014 Mathur et al.
2014/0249500 A1 9/2014 Estes et al.
2014/0257251 A1 9/2014 Bush et al.
2014/0266790 A1 9/2014 Al-Ali et al.
2014/0266794 A1 9/2014 Brown et al.
2014/0269643 A1 9/2014 Sun
2014/0276571 A1 9/2014 Ludolph
2014/0280522 A1 9/2014 Watte
2014/0294177 A1 10/2014 Shastry et al.
2014/0297329 A1 10/2014 Rock
2014/0316819 A1 10/2014 Dunsirn et al.
2014/0318639 A1 10/2014 Peret et al.
2014/0350513 A1 11/2014 Oruklu et al.
2014/0358077 A1 12/2014 Oruklu et al.
2014/0366878 A1 12/2014 Baron
2014/0371543 A1 12/2014 Steinhauer et al.
2015/0005935 A1 1/2015 Bae et al.
2015/0006907 A1 1/2015 Brouwer et al.
2015/0025503 A1 1/2015 Searle
2015/0045729 A1 2/2015 Denzer et al.
2015/0058044 A1 2/2015 Butler et al.
2015/0058960 A1 2/2015 Schmoyer et al.
2015/0066531 A1 3/2015 Jacobson et al.
2015/0081894 A1 3/2015 Blomquist
2015/0100038 A1 4/2015 McCann et al.
2015/0100787 A1 4/2015 Westin et al.
2015/0117234 A1 4/2015 Raman et al.
2015/0141955 A1 5/2015 Ruchti et al.
2015/0151051 A1 6/2015 Tsoukalis
2015/0161354 A1 6/2015 Blomquist
2015/0199192 A1 7/2015 Borges et al.
2015/0199485 A1 7/2015 Borges et al.
2015/0207626 A1 7/2015 Neftel et al.
2015/0220890 A1 8/2015 Seshadri et al.
2015/0230760 A1 8/2015 Schneider
2015/0281128 A1 10/2015 Sindhu
2015/0317891 A1 11/2015 Day et al.
2015/0325064 A1 11/2015 Downey
2015/0328396 A1 11/2015 Adams et al.
2015/0352301 A1 12/2015 Stedman et al.
2015/0365512 A1 12/2015 MacKenzie
2015/0371004 A1 12/2015 Jones
2015/0379237 A1 12/2015 Mills et al.
2016/0001003 A1 1/2016 Perazzo et al.
2016/0006695 A1 1/2016 Prodoehl et al.
2016/0015885 A1 1/2016 Pananen et al.
2016/0034655 A1 2/2016 Gray et al.
2016/0045661 A1 2/2016 Gray et al.
2016/0051749 A1 2/2016 Istoc
2016/0051751 A1 2/2016 Silkaitis et al.
2016/0063471 A1 3/2016 Kobres et al.
2016/0103960 A1 4/2016 Hume et al.
2016/0119445 A1 4/2016 Hsieh
2016/0158437 A1 6/2016 Biasi et al.
2016/0228633 A1 8/2016 Welsch et al.
2016/0241391 A1 8/2016 Fenster
2016/0277152 A1 9/2016 Xiang et al.
2016/0285876 A1 9/2016 Perez et al.
2016/0317742 A1 11/2016 Gannon et al.
2016/0350513 A1 12/2016 Jacobson et al.
2016/0378618 A1 12/2016 Cmielowski
2017/0024534 A1 1/2017 Arrizza et al.
2017/0034277 A1 2/2017 Jackson et al.

(56) References Cited

U.S. PATENT DOCUMENTS

| | | | |
|---|---|---|---|
| 2017/0054563 | A1 | 2/2017 | Verma |
| 2017/0063559 | A1 | 3/2017 | Wallrabenstein |
| 2017/0099148 | A1 | 4/2017 | Ochmanski et al. |
| 2017/0104645 | A1 | 4/2017 | Wooton et al. |
| 2017/0111301 | A1 | 4/2017 | Robinson |
| 2017/0134357 | A1 | 5/2017 | Ohlsson |
| 2017/0140134 | A1 | 5/2017 | Brough et al. |
| 2017/0146381 | A1 | 5/2017 | Eckel et al. |
| 2017/0149567 | A1 | 5/2017 | Moskal |
| 2017/0149929 | A1 | 5/2017 | Moskal |
| 2017/0214762 | A1 | 7/2017 | Swain et al. |
| 2017/0246388 | A1 | 8/2017 | Kohlbrecher |
| 2017/0258401 | A1 | 9/2017 | Volpe |
| 2017/0258986 | A1 | 9/2017 | Tsoiukalis |
| 2017/0262590 | A1 | 9/2017 | Karakosta et al. |
| 2017/0274140 | A1 | 9/2017 | Howard et al. |
| 2017/0286637 | A1 | 10/2017 | Arrizza et al. |
| 2017/0319780 | A1 | 11/2017 | Belkin et al. |
| 2017/0325091 | A1 | 11/2017 | Freeman et al. |
| 2017/0331735 | A1 | 11/2017 | Jha et al. |
| 2017/0331804 | A1 | 11/2017 | Jellison et al. |
| 2017/0351841 | A1 | 12/2017 | Moskal |
| 2018/0008772 | A1 | 1/2018 | Wehba et al. |
| 2018/0028742 | A1 | 2/2018 | Day et al. |
| 2018/0043094 | A1 | 2/2018 | Day et al. |
| 2018/0063724 | A1 | 3/2018 | Zhang et al. |
| 2018/0121613 | A1 | 5/2018 | Connely, IV et al. |
| 2018/0122502 | A1 | 5/2018 | Jones et al. |
| 2018/0126067 | A1 | 5/2018 | Ledford et al. |
| 2018/0157821 | A1 | 6/2018 | Fan |
| 2018/0181712 | A1 | 6/2018 | Ensey et al. |
| 2018/0247712 | A1 | 8/2018 | Muhsin et al. |
| 2018/0272117 | A1 | 9/2018 | Fangrow |
| 2018/0278594 | A1 | 9/2018 | Schiffman et al. |
| 2018/0317826 | A1 | 11/2018 | Muhsin et al. |
| 2018/0322948 | A1 | 11/2018 | Drost et al. |
| 2018/0359085 | A1 | 12/2018 | Dervyn |
| 2019/0006044 | A1 | 1/2019 | Brask |
| 2019/0030329 | A1 | 1/2019 | Hannaman et al. |
| 2019/0036688 | A1 | 1/2019 | Wasily et al. |
| 2019/0066831 | A1 | 2/2019 | Mairs et al. |
| 2019/0096518 | A1 | 3/2019 | Pace |
| 2019/0116160 | A1 | 4/2019 | Bhat et al. |
| 2019/0132196 | A1 | 5/2019 | Trivedi et al. |
| 2019/0147998 | A1 | 5/2019 | Ruchti et al. |
| 2019/0166501 | A1 | 5/2019 | Debates et al. |
| 2019/0172590 | A1 | 6/2019 | Vesto et al. |
| 2019/0182349 | A1 | 6/2019 | Goel et al. |
| 2019/0207965 | A1 | 7/2019 | Espinosa |
| 2019/0228863 | A1 | 7/2019 | Dharwad et al. |
| 2019/0229982 | A1 | 7/2019 | Ikuta et al. |
| 2019/0244689 | A1 | 8/2019 | Atkin |
| 2019/0244707 | A1 | 8/2019 | Becker |
| 2019/0245942 | A1 | 8/2019 | Moskal |
| 2019/0272365 | A1 | 9/2019 | Huh |
| 2019/0311803 | A1 | 10/2019 | Kohlbrecher et al. |
| 2019/0329056 | A1 | 10/2019 | Sjoquist et al. |
| 2019/0348160 | A1 | 11/2019 | Heavelyn et al. |
| 2019/0392929 | A1 | 12/2019 | Gassman |
| 2020/0023127 | A1 | 1/2020 | Simpson et al. |
| 2020/0027541 | A1 | 1/2020 | Xavier et al. |
| 2020/0027550 | A1 | 1/2020 | Xavier et al. |
| 2020/0027551 | A1 | 1/2020 | Xavier et al. |
| 2020/0051190 | A1 | 2/2020 | Kamen et al. |
| 2020/0054825 | A1 | 2/2020 | Kamen et al. |
| 2020/0118692 | A1 | 4/2020 | Booker et al. |
| 2020/0153627 | A1 | 5/2020 | Wentz |
| 2020/0206413 | A1 | 7/2020 | Silkaitis et al. |
| 2020/0220865 | A1 | 7/2020 | Finger et al. |
| 2020/0282139 | A1 | 9/2020 | Susi |
| 2020/0334497 | A1 | 10/2020 | Barrett et al. |
| 2020/0335194 | A1 | 10/2020 | Jacobson et al. |
| 2020/0351376 | A1 | 11/2020 | Moskal |
| 2020/0353167 | A1 | 11/2020 | Vivek et al. |
| 2020/0353168 | A1 | 11/2020 | Keenan et al. |
| 2020/0382323 | A1 | 12/2020 | Keselman |
| 2021/0008457 | A1 | 1/2021 | Schouviller et al. |
| 2021/0014259 | A1 | 1/2021 | Harris et al. |
| 2021/0043296 | A1 | 2/2021 | Xavier et al. |
| 2021/0045640 | A1 | 2/2021 | Poltorak |
| 2021/0085855 | A1 | 3/2021 | Belkin et al. |
| 2021/0098107 | A1 | 4/2021 | Xavier et al. |
| 2021/0105206 | A1 | 4/2021 | Jha et al. |
| 2021/0136157 | A1 | 5/2021 | Kauppila et al. |
| 2021/0252210 | A1 | 8/2021 | Day et al. |
| 2021/0358603 | A1 | 11/2021 | Xavier et al. |
| 2021/0375421 | A1 | 12/2021 | Ruchti et al. |
| 2021/0375438 | A1 | 12/2021 | Xavier et al. |
| 2021/0409362 | A1 | 12/2021 | Katis et al. |
| 2022/0023535 | A1 | 1/2022 | Day |
| 2022/0037011 | A1 | 2/2022 | Fryman |
| 2022/0037012 | A1 | 2/2022 | Fryman |
| 2022/0051777 | A1 | 2/2022 | Xavier et al. |
| 2022/0062541 | A1 | 3/2022 | Kamen et al. |
| 2022/0129452 | A1 | 4/2022 | Butler et al. |
| 2022/0139536 | A1 | 5/2022 | Xavier et al. |
| 2022/0139537 | A1 | 5/2022 | Xavier et al. |
| 2022/0139538 | A1 | 5/2022 | Xavier et al. |
| 2022/0150307 | A1 | 5/2022 | Walsh et al. |
| 2022/0165404 | A1 | 5/2022 | Vivek et al. |
| 2022/0189605 | A1 | 6/2022 | Kelly et al. |
| 2022/0191191 | A1 | 6/2022 | Brockhaus |
| 2022/0223283 | A1 | 7/2022 | Biasi et al. |
| 2022/0270736 | A1 | 8/2022 | Kohlbrecher |
| 2022/0328175 | A1 | 10/2022 | Arrizza et al. |
| 2022/0331513 | A1 | 10/2022 | Howard et al. |
| 2022/0344023 | A1 | 10/2022 | Xavier et al. |
| 2022/0375565 | A1 | 11/2022 | Xavier et al. |
| 2022/0384059 | A1 | 12/2022 | Xavier et al. |
| 2023/0009405 | A1 | 1/2023 | Xavier et al. |
| 2023/0009417 | A1 | 1/2023 | Xavier et al. |
| 2023/0145267 | A1 | 5/2023 | Xavier et al. |
| 2023/0147762 | A1 | 5/2023 | Xavier et al. |
| 2023/0231834 | A1 | 7/2023 | Carter |
| 2023/0253108 | A1 | 8/2023 | Dharwad et al. |
| 2023/0298768 | A1 | 9/2023 | Jacobson et al. |
| 2024/0047035 | A1 | 2/2024 | Ruchti et al. |
| 2024/0071609 | A1 | 2/2024 | Rohlwing |
| 2024/0293610 | A1 | 9/2024 | Jacobson |
| 2024/0321441 | A1 | 9/2024 | Rohlwing |
| 2024/0371508 | A1 | 11/2024 | Mills et al. |
| 2024/0424211 | A1 | 12/2024 | Day et al. |
| 2025/0232033 | A1 | 7/2025 | Vivek et al. |
| 2025/0381344 | A1 | 12/2025 | Wehba et al. |
| 2026/0012334 | A1 | 1/2026 | Dandekar et al. |
| 2026/0018280 | A1 | 1/2026 | Arrizza et al. |

FOREIGN PATENT DOCUMENTS

| | | |
|---|---|---|
| CA | 2 060 151 | 8/1997 |
| CA | 2 125 300 | 10/1999 |
| CA | 2 630 102 | 10/2008 |
| CA | 2 687 587 | 12/2008 |
| CA | 2 897 897 | 7/2014 |
| CA | 2 898 825 | 7/2014 |
| CA | 2 900 564 | 10/2014 |
| CA | 2 606 968 | 1/2020 |
| CN | 1759398 | 4/2006 |
| CN | 102521474 | 6/2012 |
| CN | 103816582 | 5/2014 |
| CN | 103920206 | 7/2014 |
| CN | 102300501 | 4/2015 |
| CN | 104487976 | 4/2015 |
| CN | 106960128 | 7/2017 |
| CN | 107810536 | 1/2023 |
| CO | 01110843 | 8/2003 |
| DE | 31 12 762 | 1/1983 |
| DE | 34 35 647 | 7/1985 |
| DE | 198 44 252 | 3/2000 |
| DE | 199 32 147 | 1/2001 |
| DE | 100 53 116 | 5/2001 |
| DE | 103 52 456 | 7/2005 |
| EP | 0 319 267 | 6/1989 |
| EP | 0 380 061 | 8/1990 |

(56) References Cited

FOREIGN PATENT DOCUMENTS

EP 0 384 155 8/1990
EP 0 460 533 12/1991
EP 0 564 127 6/1993
EP 0 633 035 1/1995
EP 0 652 528 5/1995
EP 0 672 427 9/1995
EP 0 683 465 11/1995
EP 0 880 936 12/1998
EP 1 050 993 11/2000
EP 1 157 711 11/2001
EP 1 174 817 1/2002
EP 0 664 102 4/2002
EP 1 197 178 4/2002
EP 0 830 775 8/2002
EP 1 500 025 4/2003
EP 1 487 171 7/2007
EP 1 933 497 6/2008
EP 2 026 223 2/2009
EP 2 113 842 11/2009
EP 2 228 004 9/2010
EP 2 243 506 10/2010
EP 2 410 448 1/2012
EP 2 742 961 6/2014
EP 2 874 087 5/2015
ES 2 371 995 1/2012
FR 2 717 919 9/1995
GB 2 285 135 6/1995
JP 04-161139 6/1992
JP 07-502678 3/1995
JP 11-500643 1/1999
JP 2000-316820 11/2000
JP 2002-531154 9/2002
JP 2003-016183 1/2003
JP 2003-296173 10/2003
JP 2003-308586 10/2003
JP 2005-021463 1/2005
JP 2005-527284 9/2005
JP 2005-284846 10/2005
JP 2006-047319 2/2006
JP 2006-520949 9/2006
JP 2007-518479 7/2007
JP 2007-525256 9/2007
JP 2008-080036 4/2008
JP 2008-516303 5/2008
JP 2008-158622 7/2008
JP 2008-529675 8/2008
JP 2009-163534 7/2009
JP 2010-502361 1/2010
JP 2011-506048 3/2011
JP 2012-011204 1/2012
JP 2012-070991 4/2012
JP 2012-523895 10/2012
JP 2014-068283 4/2014
JP 5647644 1/2015
TW 200426656 12/2004
TW I631966 8/2018
TW M589351 1/2020
TW M598505 7/2020
WO WO 84/001719 5/1984
WO WO 91/016416 10/1991
WO WO 92/010985 7/1992
WO WO 92/013322 8/1992
WO WO 94/005355 3/1994
WO WO 96/008755 3/1996
WO WO 96/025186 8/1996
WO WO 96/025963 8/1996
WO WO 98/012670 3/1998
WO WO 98/019263 5/1998
WO WO 99/051003 10/1999
WO WO 00/013580 3/2000
WO WO 00/053243 9/2000
WO WO 01/014974 3/2001
WO WO 01/033484 5/2001
WO WO 01/045014 6/2001
WO WO 01/083007 11/2001
WO WO 02/005702 1/2002
WO WO 02/036044 5/2002
WO WO 02/049153 6/2002
WO WO 02/049279 6/2002
WO WO 02/069099 9/2002
WO WO 02/081015 10/2002
WO WO 02/088875 11/2002
WO WO 03/006091 1/2003
WO WO 03/023551 3/2003
WO WO 03/050917 6/2003
WO WO 03/091836 11/2003
WO WO 03/094092 11/2003
WO WO 2004/060455 7/2004
WO WO 2004/070557 8/2004
WO WO 2004/070562 8/2004
WO WO 2004/072828 8/2004
WO WO 2005/036447 4/2005
WO WO 2005/050526 6/2005
WO WO 2005/057175 6/2005
WO WO 2005/066872 7/2005
WO WO 2007/087443 8/2007
WO WO 2007/117705 10/2007
WO WO 2007/127879 11/2007
WO WO 2007/127880 11/2007
WO WO 2008/057729 5/2008
WO WO 2008/059495 5/2008
WO WO 2008/064254 5/2008
WO WO 2008/067245 6/2008
WO WO 2008/082854 7/2008
WO WO 2008/088490 7/2008
WO WO 2008/097316 8/2008
WO WO 2008/103915 8/2008
WO WO 2008/124478 10/2008
WO WO 2008/134146 11/2008
WO WO 2009/016504 2/2009
WO WO 2009/023406 2/2009
WO WO 2009/023407 2/2009
WO WO 2009/023634 2/2009
WO WO 2009/036327 3/2009
WO WO 2009/049252 4/2009
WO WO 2010/017279 2/2010
WO WO 2010/033919 3/2010
WO WO 2010/053703 5/2010
WO WO 2010/075371 7/2010
WO WO 2010/099313 9/2010
WO WO 2010/114929 10/2010
WO WO 2010/119409 10/2010
WO WO 2010/124127 10/2010
WO WO 2010/130992 11/2010
WO WO 2010/135646 11/2010
WO WO 2010/135654 11/2010
WO WO 2010/135686 11/2010
WO WO 2011/005633 1/2011
WO WO 2011/022549 2/2011
WO WO 2012/048833 4/2012
WO WO 2012/049214 4/2012
WO WO 2012/049218 4/2012
WO WO 2012/120078 9/2012
WO WO 2012/140547 10/2012
WO WO 2012/164556 12/2012
WO WO 2012/170942 12/2012
WO WO 2013/025394 2/2013
WO WO 2013/045506 4/2013
WO WO 2014/100557 6/2014
WO WO 2014/100687 6/2014
WO WO 2014/100736 6/2014
WO WO 2014/131729 9/2014
WO WO 2014/131730 9/2014
WO WO 2015/047595 4/2015
WO WO 2015/124569 8/2015
WO WO 2016/099551 6/2016
WO WO 2016/179389 11/2016
WO WO 2017/176928 10/2017
WO WO 2017/200989 11/2017
WO WO 2019/219290 11/2019
WO WO 00/003344 1/2020
WO WO 2020/227403 11/2020
WO WO 2021/201884 10/2021
WO WO 2022/006014 1/2022

(56) References Cited

FOREIGN PATENT DOCUMENTS

| WO | WO 2022/051230 | 3/2022 |
|---|---|---|
| WO | WO 2023/044335 | 3/2023 |
| WO | WO 2023/159134 | 8/2023 |
| WO | WO 2024/196590 | 9/2024 |
| WO | WO 2025/122515 | 6/2025 |

OTHER PUBLICATIONS

Wang, Jifeng, et al. "Infusion monitoring system based on wireless transmission." 2011 4th IEEE International Symposium on Microwave, Antenna, Propagation and EMC Technologies for Wireless Communications. IEEE, 2011. (Year: 2011).*

Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.

Gutwin et al., "Gone But Not Forgotten: Designing for Disconnection in Synchronous Groupware", CSCW 2010, Feb. 6-10, 2010, Savannah, Georgia, USA., pp. 179-188.

Nojoumian et al., "Social Secret Sharing in Cloud Computing Using a New Trust Function", 2012 Tenth Annual International Conference on Privacy, Security and Trust, pp. 161-167.

Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.

Yoo et al., "Code-Based Authentication Scheme for Lightweight Integrity Checking of Smart Vehicles", IEEE Access, 2018, vol. 6, pp. 46731-46741.

Ahn et al., "Towards Scalable Authentication in Health Services", Eleventh IEEE International Workshops on Enabling Technologies: Infrastructure for Collaborative Enterprises, Jun. 2002, pp. 83-88.

Akridge, Jeannie, "New Pumps Outsmart User Error", Healthcare Purchasing News, Apr. 2011, pp. 10, <http://web.archive.org/web/20110426122450/http://www.hpnonline.com/inside/2011-04/1104-OR-Pumps.html>.

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Beard et al., "Total Quality Pain Management: History, Background, Resources", Abbott Laboratories, TQPM Survey History, available Feb. 2015 or earlier, pp. 1-3.

Bektas et al., "Bluetooth Communication Employing Antenna Diversity", Proceedings of Eight IEEE International Symposium on Computers and Communication, Jul. 2003, pp. 6.

Bellare et al., "Security Proofs for Identity-Based Identification and Signature Schemes", Lecture Notes in Computer Science, Jan. 2009, vol. 22, No. 1, pp. 18.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Braun, "Infusomat® Space and Accessories", Instructions for Use, Nov. 2010, pp. 68. <http://corp.bbraun.ee/Extranet/Infusionipumbad/Kasutusjuhendid/Vanad/Kasutusjuhend-Infusomat_Space(vers688J,inglise_k).pdf>.

Brownlee, Seth, "Product Spotlight: The Plum A+ with Hospira MedNet Infusion System", PP&P Magazine, Dec. 2005, vol. 2, No. 7, pp. 2.

Cannon, MD et al., "Automated Heparin-Delivery System to Control Activated Partial Thromboplastin Time", Circulation, Feb. 16, 1999, vol. 99, pp. 751-756.

Cardinal Health, "Alaris® Syringe Pumps" Technical Service Manual, Copyright 2002-2006, Issue 9, pp. 1-88, <http://www.frankshospitalworkshop.com/equipment/documents/infusion_pumps/service_manuals/Cardinal_Alaris_-Service_Manual.pdf>.

"CareAware® Infusion Management", Cerner Store, as printed May 12, 2011, pp. 3, <https://store.cerner.com/items/7>.

Chen et al., "Enabling Location-Based Services on Wireless LANs", The 11th IEEE International Conference on Networks, ICON 2003, Sep. 28-Oct. 1, 2003, pp. 567-572.

"Computer Dictionary", Microsoft Press, Third Edition, Microsoft Press, 1997, pp. 430 & 506.

"Context-Free Grammar", Wikipedia.org, as last modified Mar. 5, 2010 in 11 pages, <https://en.wikipedia.org/w/index.php/?title=Context-free_grammar&oldid=347915989>.

Crawford, Anne J., MSN, RNC, "Building a Successful Quality Pain Service: Using Patient Satisfaction Data and the Clinical Practice Guideline", USA, 1995, pp. 1-6.

Crocker et al., "Augmented BNF for Syntax Specifications: ABNF", Network Working Group, Standards Track, Jan. 2008, pp. 16.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

Davies, T., "Cordless Data Acquisition in a Hospital Environment", IEE Colloquium on Cordless Computing—Systems and User Experience, 1993, pp. 4.

Dayhoff et al., "Medical Data Capture and Display: The Importance of Clinicians' Workstation Design", AMIA, Inc., 1994, pp. 541-545.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

Doesburg et al., "Improved Usability of a Multi-Infusion Setup Using a Centralized Control Interface: A Task-Based Usability Test", Aug. 11, 2017, PLoS ONE, vol. 12, No. 8, pp. 10.

"Download", Free On-Line Dictionary of Computing, as archived Jun. 16, 2010 in 1 page, http://web.archive.org/web/20100616010314/https://foldoc.org/download.

East PhD et al., "Digital Electronic Communication Between ICU Ventilators and Computers and Printers", Respiratory Care, Sep. 1992, vol. 37, No. 9, pp. 1113-1122.

Edworthy, Judy, "Medical Audible Alarms: A Review", Journal of the American Medical Informatics Association, vol. 20, No. 3, 2013, pp. 584-589.

Einhorn, George W., "Total Quality Pain Management: A Computerized Quality Assessment Tool for Postoperative Pain Management", Abbott Laboratories, Chicago, IL, Mar. 2, 2000, pp. 1-4.

Eskew et al., "Using Innovative Technologies to Set New Safety Standards for the Infusion of Intravenous Medications", Hospital Pharmacy, 2002, vol. 37, No. 11, pp. 1179-1189.

Felleiter et al., "Data Processing in Prehospital Emergency Medicine", International journal of Clinical Monitoring and Computing, Feb. 1995, vol. 12, No. 1, pp. 37-41.

"File Verification", Wikipedia.org, as last modified Oct. 11, 2011 in 2 pages, <https://en.wikipedia.org/w/index.php?title=File_verification&oldid=455048290>.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

Gabel et al., "Camp: A Common API for Measuring Performance", 21st Large Installations System Administration Conference (LISA '07), 2007, pp. 49-61.

Gage et al., "Automated Anesthesia Surgery Medical Record System", International Journal of Clinical Monitoring and Computing, Dec. 1990, vol. 7, No. 4, pp. 259-263.

Galt et al., "Personal Digital Assistant-Based Drug Information Sources: Potential to Improve Medication Safety", Journal of Medical Library Association, Apr. 2005, vol. 93, No. 2, pp. 229-236.

(56) References Cited

OTHER PUBLICATIONS

Gardner, Ph.D. et al., "Real Time Data Acquisition: Recommendations for the Medical Information Bus (MIB)", 1992, pp. 813-817.
"General-Purpose Infusion Pumps", Health Devices, EXRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", <http://www.trackingsystem.com/forbusinesses/corporate-trackingsystem/1098-gps-tracker-formedicalequipment.html>, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Numbers from 3000 to 59,999", Technical Service Manual, Graseby Medical Ltd., Apr. 2002, Issue A, pp. 71.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, <www.hospira.com/products/gemstar_painmanagement.aspx>, Jan. 28, 2010, pp. 1-2.
Huang et al., "Secure Identity-Based Data Sharing and Profile Matching for Mobile Healthcare Social Networks in Cloud Computing", vol. 6, Jul. 2018, pp. 36584-36594.
Introducing Abbott TQPM (Total Quality Pain Management), Abbott Laboratories, Abbott Park, IL, May 2000, pp. 1-4.
"Infusion Pump", Wikipedia.org, as last modified Mar. 27, 2014, in 3 pages, <https://web.archive.org/web/20140703024932/https://en.wikipedia.org/wiki/Infusion_pump>.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety In Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.
Li et al., "Hijacking an Insulin Pump: Security Attacks and Defenses for a Diabetes Therapy System", 2011 IEEE 13th International Conference on e-Health Networking, Applications and Services, 2011, pp. 150-156.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
"McKesson Automation and ALARIS Medical Systems Developing Point-of-Care Bar Coding Solution to Improve IV Medication Safety", PR Newswire, NY, Dec. 9, 2002, pp. 4.
Medfusion™, "Medfusion Syringe Infusion Pump Model 4000", Operator's Manual, Software Version V1.1, Sep. 2011, pp. 154. <http://www.medfusionpump.com/assets/literature/manuals/Operators_Manual_4000_40-5760-51A.pdf>.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Michienzi, Kelly, "Managing Drug Library Updates", Pharmacy Purchasing Products, https://www.pppmag.com/article/1061, Feb. 2012, vol. 9, pp. 22-23.
Micrel Medical Devices, "MP Daily +" <http://web.archive.org/web/20130803235715/http://www.micrelmed.com/index.aspx?productid=9> as archived Aug. 3, 2013 in 1 page.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
Omnilink Systems, Inc., "Portable Medical Equipment Tracking", <http://www.omnilink.com/portablemedicalequipmenttracking/>, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, June 30-Jul. 4, 2009, pp. 8.
Philips, "IntelliSpace Event Management and IntelliVue Patient Monitoring", Release 10, 2011, <http://incenter.medical.philips.com/doclib/enc/fetch/2000/4504/577242/577243/577247/582646/583147/

(56) References Cited

OTHER PUBLICATIONS

8359175/Philips_Patient_Monitoring_and_IntelliSpace_Event_Management_Interoperability.pdf%3fnodeid%3d8508574%26vernum%3d-2>, pp. 2.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", May 15, 2008, pp. 63. <https://usme.com/content/manuals/sigma-spectrum-operator-manual.pdf>.
"Sigma Spectrum: Operator's Manual", Oct. 2009, pp. 72. <http://static.medonecapital.com/manuals/userManuals/Sigma-Spectrum-Operator-Manual-October-2009.pdf>.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. <http://www.thomasland.com/hpj4209-832.pdf>.
Slack, W.V., "Information Technologies for Transforming Health Care", <https://www.andrew.cmu.edu/course/90-853/medis.dir/otadocs.dir/03ch2.pdf>, Ch. 2, 1995, pp. 29-78.
Smith, Joe, "Infusion Pump Informatics", CatalyzeCare: Transforming Healthcare, as printed May 12, 2011, pp. 2.
Sodders, Lisa, "VA Center Keeps Medicine in Right Hands", The Capital-Journal, Dec. 4, 1999, pp. 1-2.
"Software Versioning", Wikipedia.org, dated Oct. 16, 2011 in 11 pages, <https://en.wikipedia.org/w/index.php?title=Software_versioning&oldid=455859110>.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
"TCG TPM v2.0 Provisioning Guidance", Reference, Version 1, Revision 1, Mar. 15, 2017, pp. 1-43.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
Banerjee et al., "Token-Based Authentication Techniques on Open Source Cloud Platforms", Sistemas y Telemática, vol. 16, No. 47, 2018, pp. 17.
Chan, Katherine Yin-Yee. "Mitigating Risks Associated with Secondary Intravenous Infusions: An Empirical Evaluation of a Technology-Based, Training-Based, and Practice-Based Intervention." Order No. 1570719 University of Toronto (Canada), 2013. Ann Arbor: ProQuest. Web. Nov. 23, 2024, pp. 182.
Cloudflare, "What Happens in a TLS Handshake? | SSL Handshake", as archived May 19, 2020, https://web.archive.org/web/20200519192121/https:/www.cloudflare.com/en-au/learning/ssl/what-happens-in-a-tls-handshake/, 4 pages.
Fan et al., "Smart Medication Delivery Systems: Infusion Pumps", Supplementary Report, Healthcare Human Factors, Feb. 26, 2010, pp. 94.
Murphy, Robert, "The Design of Safety-Critical Medical Infusion Devices", May 30, 2007, Doctor of Philosophy submission, pp. 317.
O'Brien et al., "Securing wireless infusion pumps", NIST Special Publication (1800): 8B, 2018, pp. 85.
Rahmani et al., "Smart e-Health Gateway: Bringing Intelligence to Internet-of-Things Based Ubiquitous Healthcare Systems", 2015

(56) References Cited

OTHER PUBLICATIONS

12th Annual IEEE Consumer Communications and Networking Conference (CCNC), Jul. 2015, pp. 826-834.
Sabir et al., "Authentication Model Based on JWT and Local PKI for Communication Security in Multi-agent Systems", International Conference Europe Middle East & North Africa Information Systems and Technologies to Support Learning. Springer, Cham, 2019, pp. 469-479.
Sethia et al., "Security Framework for Portable NFC Mobile Based Health Record System", Oct. 2016, IEEE 12th International Conference on Wireless and Mobile Computing, Networking and Communications, pp. 1-8.
Stack Exchange, "Avoiding SSL handshake for each call", as archived Sep. 22, 2021, https://web.archive.org/web/20210922184153/https:/security.stackexchange.com/questions/56623/avoiding-ssl-handshake-for-each-call, 3 pages.
Marinkovic et al., "Ultra Low Power Signal Oriented Approach for Wireless Health Monitoring", Sensors, 2012, vol. 12, pp. 7917-7937.

* cited by examiner

600

$$\text{MaxIndexNumber}$$

$$* \left( \left( \frac{(\text{HmssMaxCPU\%} + \text{HmssAvgCPU\%})}{2} * \text{HmssCPU\%} \right) + \left( \frac{(\text{SqlMaxCPU\%} + \text{SqlAvgCPU\%})}{2} * \text{SqlCPU\%} \right) + f(x) \right.$$

$$= \begin{cases} \frac{\text{NumOfJMSMsg}}{\text{NumOfInfusers} * 10} * \text{NumOfJMSMsg\%}, & \text{NumOfJMSMsg} < \text{NumOfInfusers} * 10 \\ \text{NumOfJMSMsg\%}, & \text{Otherwise} \end{cases}$$

$$+ \left( \left( f(x) = \begin{cases} \frac{\text{AvgHmssPQL}}{\text{NumHmssCore} * 1.5}, & \text{AvgHmssPQL} < \text{NumHmssCore} * 1.5 \\ 1, & \text{Otherwise} \end{cases} \right) * f(x) = \begin{cases} \text{HmssPQL\%}, & \text{Svr Cfg} = \text{Distributed} \\ (\text{HmssPQL\%} + \text{SqlPQL\%}), & \text{Otherwise} \end{cases} \right)$$

$$+ \left( \left( f(x) = \begin{cases} \frac{\text{HmssDQL}}{1.75}, & \text{HmssDQL} \le 2 \\ 1, & \text{Otherwise} \end{cases} \right) * f(x) = \begin{cases} \text{HmssDQL\%}, & \text{Svr Cfg} = \text{Distributed} \\ (\text{HmssDQL\%} + \text{SqlDQL\%}), & \text{Otherwise} \end{cases} \right) + f(x)$$

$$= \begin{cases} f(x) = \begin{cases} \frac{\text{SqlDQL}}{1.75} * \text{SqlDQL\%}, & \text{SQLDQL} \le 2 \\ \text{SqlDQL\%}, & \text{Otherwise} \end{cases} + f(x) = \begin{cases} \frac{\text{AvgSQLPQL}}{\text{NumSQLCore} * 1.5} * \text{HmssPQL\%}, & \text{AvgSqlPQL} < \text{NumSQLCore} * 1.5, \\ \text{HmssPQL\%}, & \text{Otherwise} \end{cases} & \text{Svr Cfg} = \text{Distributed} \\ 0, & \text{Otherwise} \end{cases}$$

$$\left. + \left( \frac{\text{MemUsed}}{\text{MaxMem}} \right) * \text{MemUsage\%} \right)$$

| Phases | Vanilla Symbiq | Vanilla Symbiq w/ IVCI |
|---|---|---|
| 5.5 Baseline | 74.037 | N/A |
| Phase 1 | 71.067 | 70.285 |
| Phase 2 | 66.476 | 71.847 |
| Phase 3 | 46.344 | 52.424 |
| Phase 4 | 51.490 | 53.667 |
| Phase 5 (5.81.002) | N/A | 57.473 |
| Customer X | N/A | 5.954 |

MEDICAL DEVICE SYSTEM PERFORMANCE INDEX

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

As technology becomes increasingly computer-based, medical devices are more commonly utilizing electronic features that interact with a larger system. For example, a hospital information system can transfer data to and from a medication management unit, which can facilitate communication with a plurality of specific hospital beds or medical devices to record and transmit treatment parameters for patients. In another example, medical devices can be programmed to notify clinicians when certain alarms or occurrences of a particular event are triggered. Furthermore, medical facilities routinely utilize electronic databases such as drug libraries and bar code systems to improve the administration of medication and prevent human errors. Thus, an electronic network system can be quite extensive and complex in a typical hospital setting due to the interaction of the various system components.

Infusion pumps are one type of medical device and are used for intravenous delivery of medicines such as insulin, analgesics, sedatives, vasopressors, heparin and anti-arrhythmics to patients. Correct delivery of these medications is important for avoiding adverse events, particularly in critically ill patients. Smart infusion pumps, which include drug libraries and integrated decision support software in their medication delivery systems, have decreased errors in administration of medications by incorporating features such as hard and soft alarm limits, clinician messaging, and medication barcode input. Smart pumps are also able to utilize electronic medical records and inputs customizable for specific clinical care areas, wards or to improve safety for individual patients. Other infusion systems have incorporated features for a specific disease, such as algorithms to change the rates of insulin delivery based on a patient's glucose level, or to offer procedures specifically for advanced cardiac life support.

SUMMARY OF THE INVENTION

A distributed network system and method includes a processing unit configured to manage safety data for a plurality of medical devices, a database software component in communication with the processing unit, and a monitoring software component in communication with the processing unit. The monitoring software component is configured to monitor a number of messages between a number of medical devices and the processing unit, to process performance parameters to generate an overall performance index, and to generate an output that is viewable by a user. The output includes relative contributions of each of the performance parameters to the overall performance index, where the overall performance index is generated using a weighting factor associated with each of the performance parameters. The performance parameters include the number of messages waiting to be processed, which has the largest weighting factor, and a disk queue length, which has the smallest weighting factor.

BRIEF DESCRIPTION OF THE DRAWINGS

Each of the aspects and embodiments of the invention described herein can be used alone or in combination with one another. The aspects and embodiments will now be described with reference to the attached drawings.

FIG. 6 shows an equation for calculating a performance index, in one embodiment;

DETAILED DESCRIPTION OF THE PREFERRED EMBODIMENT

Figure 1:
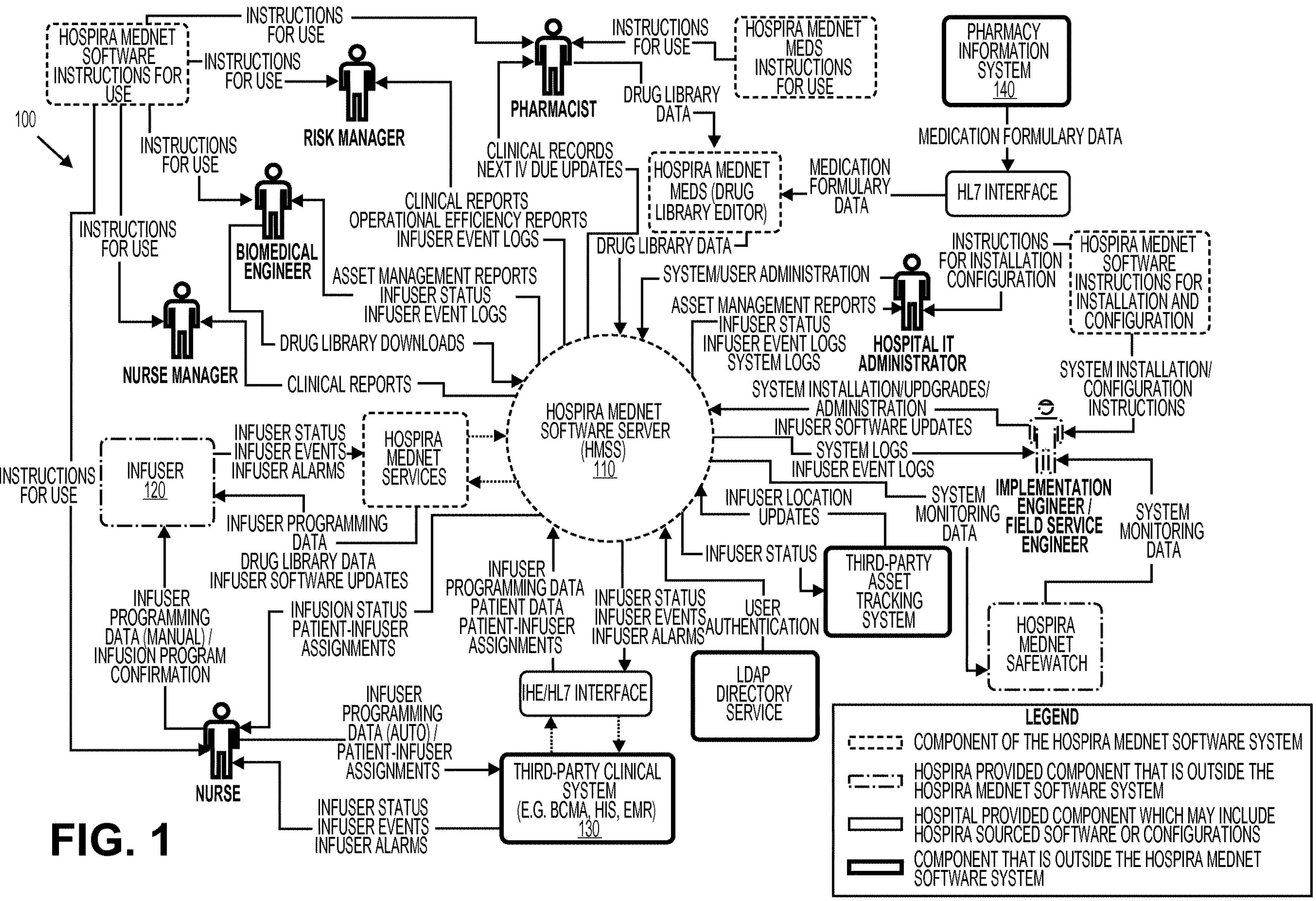
FIG. 1 shows a system context diagram of an exemplary medical device network system.

FIG. 1 provides a system context diagram of an exemplary medical device network system 100. The system 100 includes a medical device management component 110 that is configured to manage safety data for a plurality of medical devices. In this figure, the management component 110 is shown as Hospira MedNet™ Software, manufactured and sold by Hospira, Inc., the assignee of the present disclosure. However, other medical device management systems may be utilized instead. Similarly, the medical devices described herein shall be referred to as infusers or infusion pumps; however, other types of medical equipment with electronic data interfaces such as hospital beds, patient monitoring units, or surgical devices are applicable.

In FIG. 1, the medical device management component 110 has a software server (Hospira MedNet™ Software Server "HMSS") that interfaces to a medical device such as an infuser 120, and also provides communication with other systems such as a third-party clinical system 130 and a pharmacy information system 140. Third-party clinical system 130 may be, for example, a bar code medication administration (BCMA), hospital information system (HIS), or electronic medical record (EMR). Thus, the medical device management component 110 manages information, such as IV infusion information, for medical treatment of a patient and helps to reduce medication errors, improve quality of care, streamline clinical workflows and deliver potential cost savings.

The configurations for medical device network system 100 can vary widely in scope, depending on many factors. For instance, the size of the facility in which network system 100 is used may vary from a private practice, with a few medical devices 120, to a large hospital with a large number of devices 120 linked to the network. Similarly, the hardware associated with the system 100 can vary widely in configuration such as in the number of processors, the memory capacity, and processing capability of the hardware. Furthermore, the amount of transactions generated within the system 100 will depend on the operational needs of that particular facility. Thus, it would be desirable to be able to evaluate or to predict the performance of a particular configuration of a medical device management system to improve or optimize the configuration for a particular application or facility.

Figure 2:
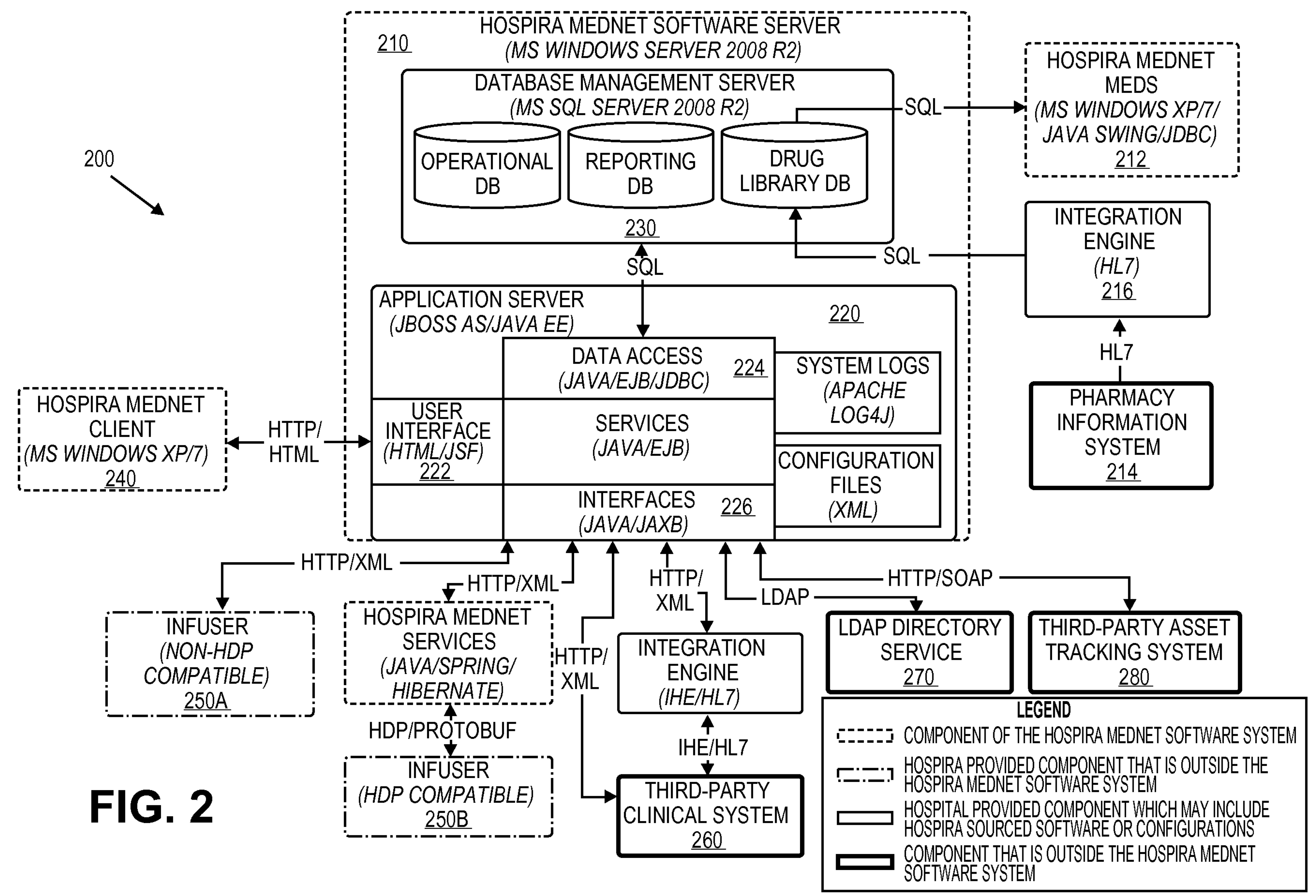
FIG. 2 is a technical block diagram of a medical device network, in one embodiment.

FIG. 2 is a technical block diagram of an embodiment of a medical device network system 200 that includes a medical device management component 210 (e.g., Hospira MedNet™ Software Server) having an application server 220 and a database management server 230. The application server 220 is a processing unit that may operate on, for example, a JBoss™ or Java™ platform. The database management server 230 is in communication with the application server 220 and may be operate using any database programming language, for example, Structured Query Language (SQL). In this embodiment, database server 230 communicates with application server 220, with a drug library 212 (embodied here as Hospira MedNet™ Meds™), and/or with a pharmacy information system 214 via an integration engine 216. Thus, application server 220 manages data for medical devices 250*a* and 250*b* by accessing medication information from drug library 212 and pharmacy information system 214, and by interfacing with database 230 to retrieve and store data.

Application server 220 may include various components such as a user interface 222 for communicating with a client device 240, a data access component 224 to communicate with the database management server 230, and additional interfaces 226. Additional interfaces 226 may be configured to communicate with medical devices 250*a/b*, a third-party clinical system, a lightweight directory access protocol (LDAP) directory service 270, and a third-party asset tracking system 280. Medical devices 250*a* and 250*b*, embodied here as infusers, are outside the medical management system 210 and may interface with medical management system 210 using protocols that are health device profile (HDP) compatible or non-HDP compatible.

In FIG. 2, it can be seen that system 200 involves many mutually, dependent programs that operate within an interdependent computer system. Since medical device management component 210, medical devices 250*a/b*, third-party clinical system 260, and other components may each be provided from different suppliers, the communication between all the various components may require interfacing between multiple program languages and communication protocols. For example, in FIG. 2, medical network system 200 accommodates SQL and Java™ languages, using HTTP/HTML, HTTP/XML, HTTP/SOAP and LDAP. Thus, the present systems and methods provide evaluation of medical device network system in which the system involves various platforms integrated together. Furthermore, the present systems and methods provide performance data for the overall network, and not just individual transactions. Data is gathered from the network and then processed and presented in a manner that allows a user to identify where bottlenecks or problems are occurring in the system.

The ability to evaluate or predict the performance of the system for various hardware and software configurations of a medical device system network, as described above, requires the integration of many parameters. Furthermore, identifying what parameters to evaluate, and how to integrate them to produce meaningful metrics can be burdensome. In the present disclosure, a performance index is described that not only derives an overall index value for a medical device network system, but also provides information on the relative contributions of the various performance parameters to the index. These relative contributions can be outputted, for example, in a graphical display to facilitate interpretation of the analysis by a user. The ability to view the impact of the performance parameters on the overall system enables a user to correct for detected problems. For example, a user can make adjustments to the medical device management software (e.g., Hospira MedNet™) to address specific problems. In one exemplary adjustment, a user may, tune a SQL statement to help it improve the utilization of SQL to retrieve data, to further minimize latency around processing of messages. In other types of adjustments, the machine configuration within a computer may be altered to improve processing of messages, such as by modifying the hardware to increase the number of cores and threads. Thus, the evaluation can demonstrate value from a total cost of ownership standpoint, such as by identifying whether hardware for a particular network system needs to be changed to meet performance goals. For instance, the thread count, core count and memory of a system could be simulated and evaluated to accommodate a desired number of active objects running at the same time. The evaluations provided by the present methods can also enable performance comparisons of the impact that various medical device products have on system performance when connected to the network.

The performance index is generated by a monitoring software component that is in communication with the processing unit of the medical device management component. The monitoring software component is configured to i) monitor a number of messages between a number of medical devices and the processing unit, ii) process performance parameters to generate an overall performance index, and iii) generate an output that is viewable by a user, wherein the output includes relative contributions of each of the performance parameters to the overall performance index. The processing unit, the database software component, and the monitoring software component are housed on at least one computer. For example, in some embodiments the processing unit, the database software component and the monitoring software component may all be on separate computers. In other embodiments, the medical device management system processing unit and the database software component may be on one computer while the monitoring software component may be housed on a separate computer. In still further embodiments, the database software component, monitoring software component, and medical device management system processing unit are all located on separate computers.

Figure 3:
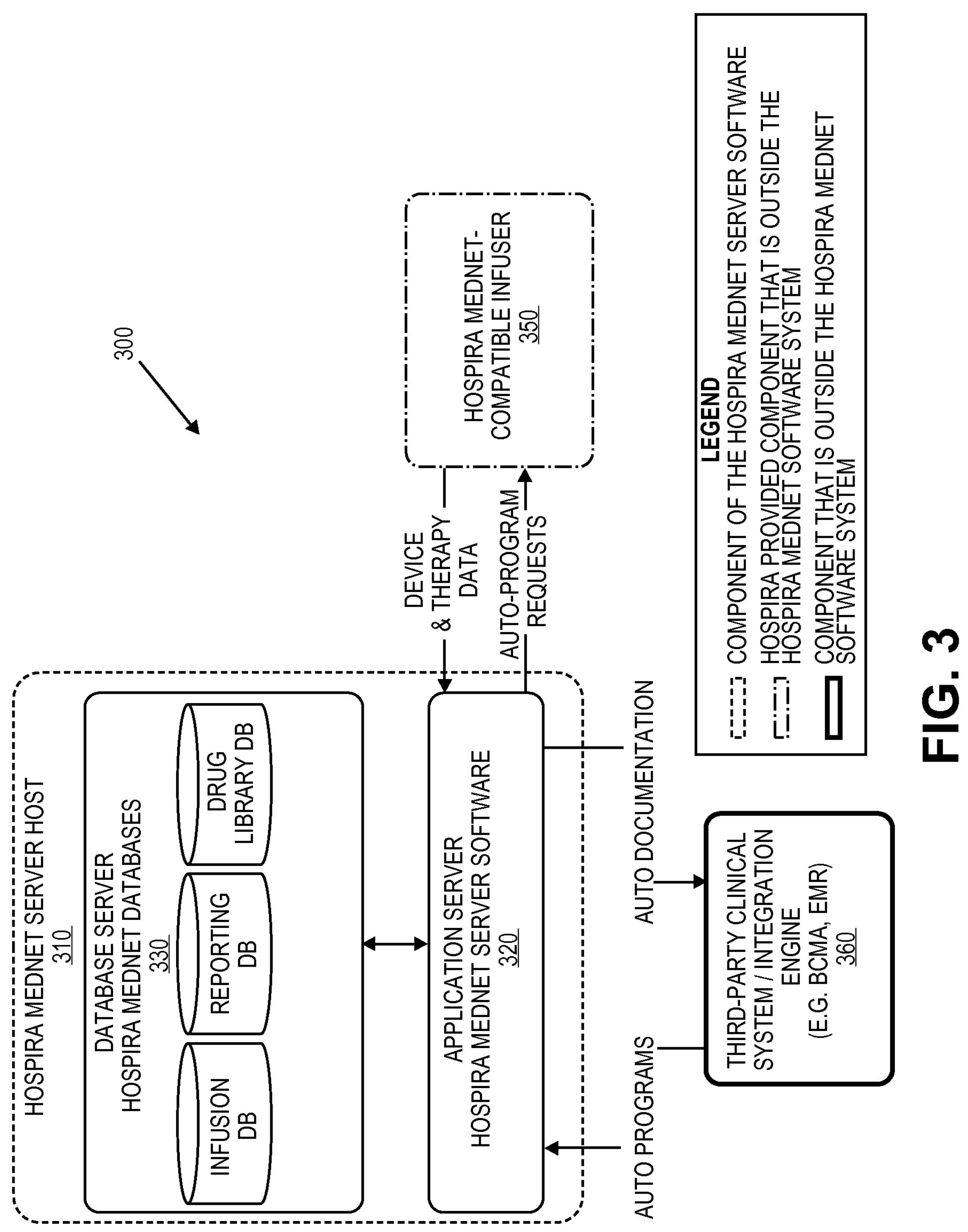
FIG. 3 is an exemplary block diagram of a single server configuration.

FIG. 3 depicts a diagram of a medical device network system 300 in a single server configuration. Similar to the previous figures, medical device network system 300 has a medical device management system 310 that includes an application server 320 and a database server 330. The application server 320 is a processing unit that is in communication with and is hosted together on a single server with database server 330. Application server 320 is also in communication with third-party clinical system/integration engine 360, as well as with medical device 350, which is embodied here as an infusion pump. Medical device 350 in diagram 300 may refer to one or more medical devices. Third-party clinical system 360 may provide auto programs to application server 320, and may receive auto documentation from application server 320. For instance, auto programs and auto documentation may assist in automatically programming the medical device 350 and charting of that information. Medical device 350 may receive auto program requests from application server 320, and may send device and therapy data to application server 320.

Figure 4:
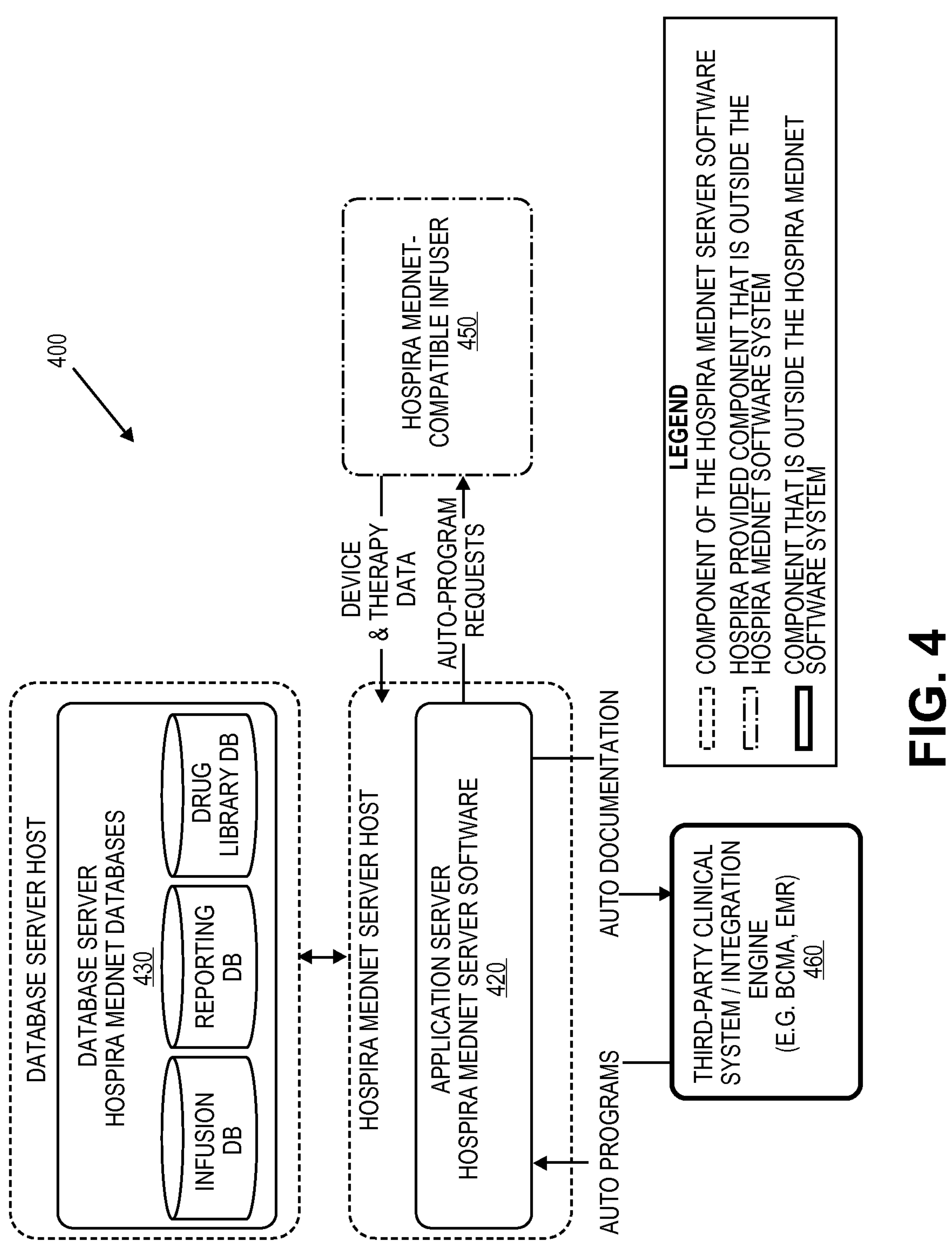
FIG. 4 is an exemplary block diagram of a distributed server configuration.

FIG. 4 is similar to FIG. 3 but for a medical device network system 400 having a distributed server configuration. That is, application server 420 is housed on a first computer, while database server 430 is on a second computer. Medical device 450 and third-party clinical system/integration engine 460 are the same as in FIG. 3.

In a network system, an important aspect of performance is the efficiency of processing messages through the system. This efficiency can be evaluated in many ways, depending on what measurement elements are utilized in the calculations. In the development of the present methods, parameters that affect performance were first identified, such as the central processing unit (CPU) consumption, processor queue length (PQL), disk queue length (DQL), and number of messages waiting in the medical device management software queue. For the purposes of this disclosure, the medical device management software will be described as a Java Messaging Service™ (JMS) system, although other types of programs may be substituted. After the performance parameters were identified, they were placed in order of importance. In one embodiment, the categories were ordered as JMS backlog, CPU, Memory usage, then Disk Input/Output. Based on their importance, a weighting percentage was distributed accordingly, for formulation of the performance index.

In some embodiments, the monitoring software component monitors actual traffic—that is, messages—within an operational medical device network system. The output results of performance index and contributions of the various performance parameters can then be used to identify, for instance, if the system has sufficient capacity for a certain number of medical devices, and where bottlenecks in system efficiency may be occurring. In other embodiments, the monitoring software simulates a number of medical devices that would be connected to the network, and simulates a number of messages generated by the medical devices. For such a simulation, the monitoring software enables a user to, for example, vary an anticipated number of medical devices connected to the network and the number of messages generated from the medical devices, to determine performance for projected configurations and optimize the system accordingly. For simulation scenarios, medical device 350 or 450 of FIGS. 3 and 4 may be a server that houses the monitoring software, external to the medical device management component, to simulate the load on the medical device network system during operation.

Performance parameters that are used for calculating system performance metrics involve factors related to the management software component, the database component, and the medical devices. In this disclosure, the following terminology shall be used:

CPU=Central Processing Unit or Processor of a machine.

DQL=Disk Queue Length. The average disk queue lengths represent the average number of both outstanding read and write requests at a given time.

HMSS=Hospira MedNet™ Server Suite, which represents a medical device management component, such as a software program housed on a first processing unit.

JMS=Java Messaging Service™. This is a set of interfaces for sending messages between two or more clients. [0030] PQL=Processor Queue Length. The processor queue length is an indicator for the number of threads waiting to be processed.

SQL=Structured Query Language. In this disclosure, the term shall be used to reference the database server, although in other embodiments, other database languages may be substituted.

Perfmon=Windows™ Performance Monitor. This is a tool within the server that holds the Hospira Mednet™ software, that is used to collect the data and statistics of the network system. In other embodiments, other tools such Unix™ or Linux™ equivalents are possible.

The following variables for calculation of the performance index in this disclosure are described below:

HmssCPU=Observed HMSS CPU consumption. (CPU of the medical device management system) The consumption value is normalized to a percentage, such as 45% CPU Usage.

HmssPQL=Observed HMSS processor queue length. (PQL of the medical device management system) This value is taken from Perfmon. A maximum allowable value is set according to desired goals, such as number of cores*1.5. For example, if the CPU of the machine/VM have 4 cores, the maximum allowable queue length is 6. In other embodiments, the allowable tolerance may be 2-4 times the number of cores.

HmssDQL=Observed HMSS disk queue length. (DQL of the medical device management system) This value is taken from Perfmon. A maximum allowable value is set according to desired goals, such as a recommended queue length of less than 2. Higher values portend application performance degradation due to input/output (110) latency.

Sq1CPU=Observed SQL (or other database) CPU consumption. This is the same as HmssCPU but measured for the database server.

Sq1PQL=Observed SQL (or other database) processor queue length. This is the same as HmssPQL but measured for the database server.

Sq1DQL=Observed SQL (or other database) disk queue length. This is the same as HmssDQL but measured for the database server.

NumOfJMSMsg=Observed number of JMS messages waiting to be processed. This value is taken from the JMS queue. A maximum allowable value is set according to desired goals, such as the maximum value being the Total Number of Infusers*10. For example, if a test consists of 100 infusers, JMS backlog of 1000 or more as measured at the end of the test is considered a failure.

MemUsage=HMSS (or other medical device management system) memory usage.

MaxIndexNumber=The total maximum value used for the Performance Index. In some embodiments, a lower value indicates better performance.

Figure 5:
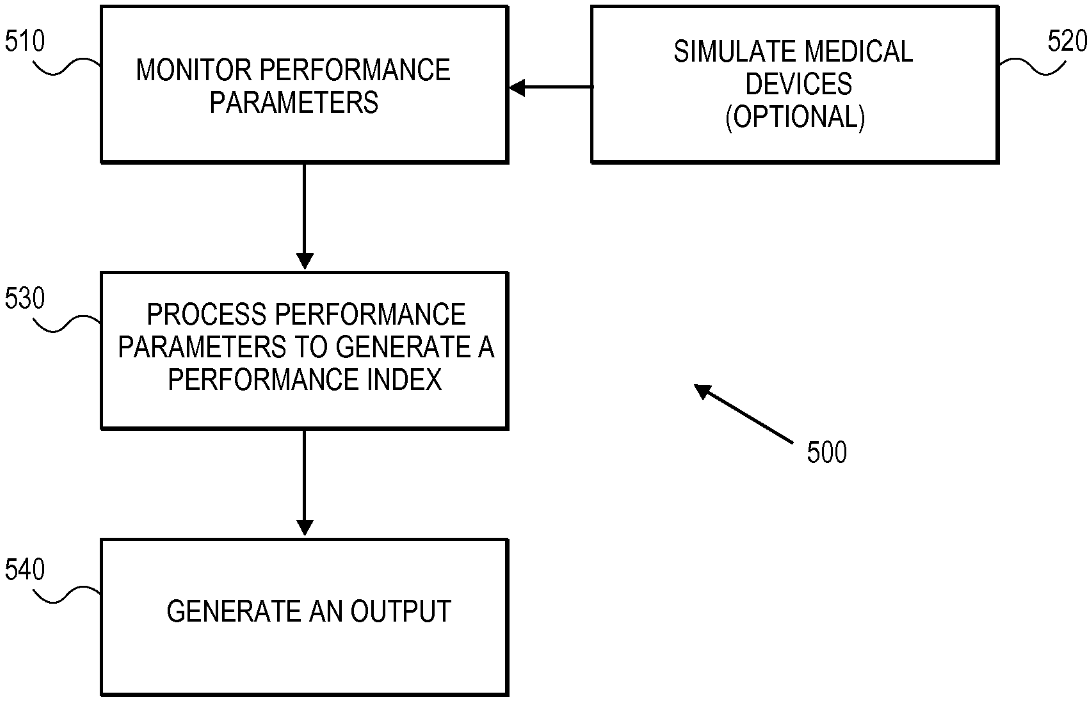
FIG. 5 shows an exemplary flow chart for a method of generating a performance index.

FIG. 5 shows an exemplary flow diagram 500 of the monitoring software in some embodiments. In step 510, performance parameters are monitored and gathered for evaluation. Step 510 may be conducted by custom software or by pre-packaged software. In one embodiment, step 510 utilizes Windows™ PerfMon to specify collector sets, such as queue length. Use of a program such as PerfMon can enable the monitoring software to be transportable to any type of server. The performance parameters may be gathered from a distributed network, such as a network including processing unit acting as a medical device management server, a database server, medical devices outside the medical device management server, and third-party interfaces. In step 520, the medical devices can optionally be simulated by the monitoring software program, such as by simulating the number of medical devices connected to the network, the type of devices, and the number of messages being generated by the devices. Because different types of devices, such as different models of infusions pumps, manifest traffic in different ways, the monitoring software can be programmed for a user to test different types and combinations of these devices. In other embodiments where performance of an actual physical system is being evaluated, step 520 may be omitted.

In step 530, the data is processed. For example, a set of data gathered within a specified time period may be aggregated for calculation of a set of performance metrics. Calculation of the performance parameters utilizes weighting factors associated with each performance parameter, as shall be described in more detail below, to generate an overall performance index. In step 540, an output is generated that is viewable by a user. The output includes relative contributions of the performance parameters to the overall performance index. For example, the output may take the form of numerical data tables, vertical or horizontal bar charts, such as stacked or grouped columns.

Calculation of performance parameters, such as in step 530 of FIG. 5, shall now be described in more detail. FIG. 6 shows an equation 600 for calculating a performance index, in one embodiment. In equation 600, the functions f(x) are defined by the entities to the right of that, indicated by curly braces. The equation can be generalized as $$\left(MaxIndexNumber * \sum \frac{NotedCategoryTakenResult}{MaxCateboryAllowedValue} * \text{Category Weighted \%}\right).$$

That is, the performance index is generated by summing entities for all the performance parameters, the entity for each performance parameter being the performance parameter value divided by a maximum allowed value and multiplied by the weighting factor associated with the performance parameter. For example, the first entity in equation 600 adds the maximum and average HMSS CPU data, divides it by the allowed value of 2, and multiplies the total by its weighting factor "HmssCPU %." The other performance parameters of Sq1CPU, Number of JMS Messages, HmssPQL, HmssDQL, Sq1DQL and Memory Usage are similarly calculated and summed. Note that the equation takes into account the server configuration format. Thus, for non-distributed scenarios the PQL and DQL are taken only once and the weighted percentage is combined. For example, if the system PQL=2.2 in a four core all-in-one machine, the formula would be (2.2/(4*1.5))*(0.125+0.1).

The weighting factor for each variable is carefully determined in relation to its contribution on system performance. A set of weighting factors, in some embodiments, is listed in Table 1 below, with a description of the weighting factors being presented in the subsequent paragraphs.

TABLE 1

| Variable | Weighting Factor |
|---|---|
| HmssCPU | 12.5% |
| HmssPQL | 12.5% |
| HmssDQL | 5% |
| SqlCPU | 12.5% |
| SqlPQL | 12.5% |
| SqlDQL | 5% |
| NumOfJMSMsg | 30% |
| MemUsage | 10% |
| MaxIndexNumber | 100% |

NumOfJMSMsg—This was deemed to have the largest weighting factor, such as about 30%, because the majority of the functionality of the Hospira MedNet™ software has to do with message processing and the timeliness of when the messages are processed. An example is processing status messages sent by the infuser and in turn sending updated statuses to a third party integrator. If there is a build up of messages and a messages stays in the queue longer than desired, by the time the message is sent out it is already stale. The JMS message counter can also reveal issues within Hospira MedNet™ software that otherwise seems like Hospira MedNet™ is performing optimally. There are times when both CPU and PQL counters are low but JMS number is high. This is usually a clear indicator of a deadlock on either the JAVA side, SQL side or both.

CPU and PQL—These factors in Table 1 have intermediate weighting, such as about 12.5%. Raw processing and how long a process needs to wait for CPU time are the next factors. In an optimal operating environment when there are no blockages CPU is usually the limiting factor. The weighting is equally spread between CPU and PQL on both HMSS and SQL servers.

MemUsage—MemUsage has intermediate weighting, such as about 10%. This was deemed important because in order to have peak performance, having memory and not needing to use I/O is very crucial. A weighting factor of about 10% provides a good indicator if HMSS has a memory leak. Memory leak deals with memory clean-up and allocation, which can cause a system to fail if memory space becomes insufficient.

DQL—In the embodiment of Table 1 DQL has the smallest value, such as about 5%. This weighting will reveal any I/O bottlenecks in the system when running Hospira MedNet™ software, providing a relative indication of the importance of other problems.

Figure 7:
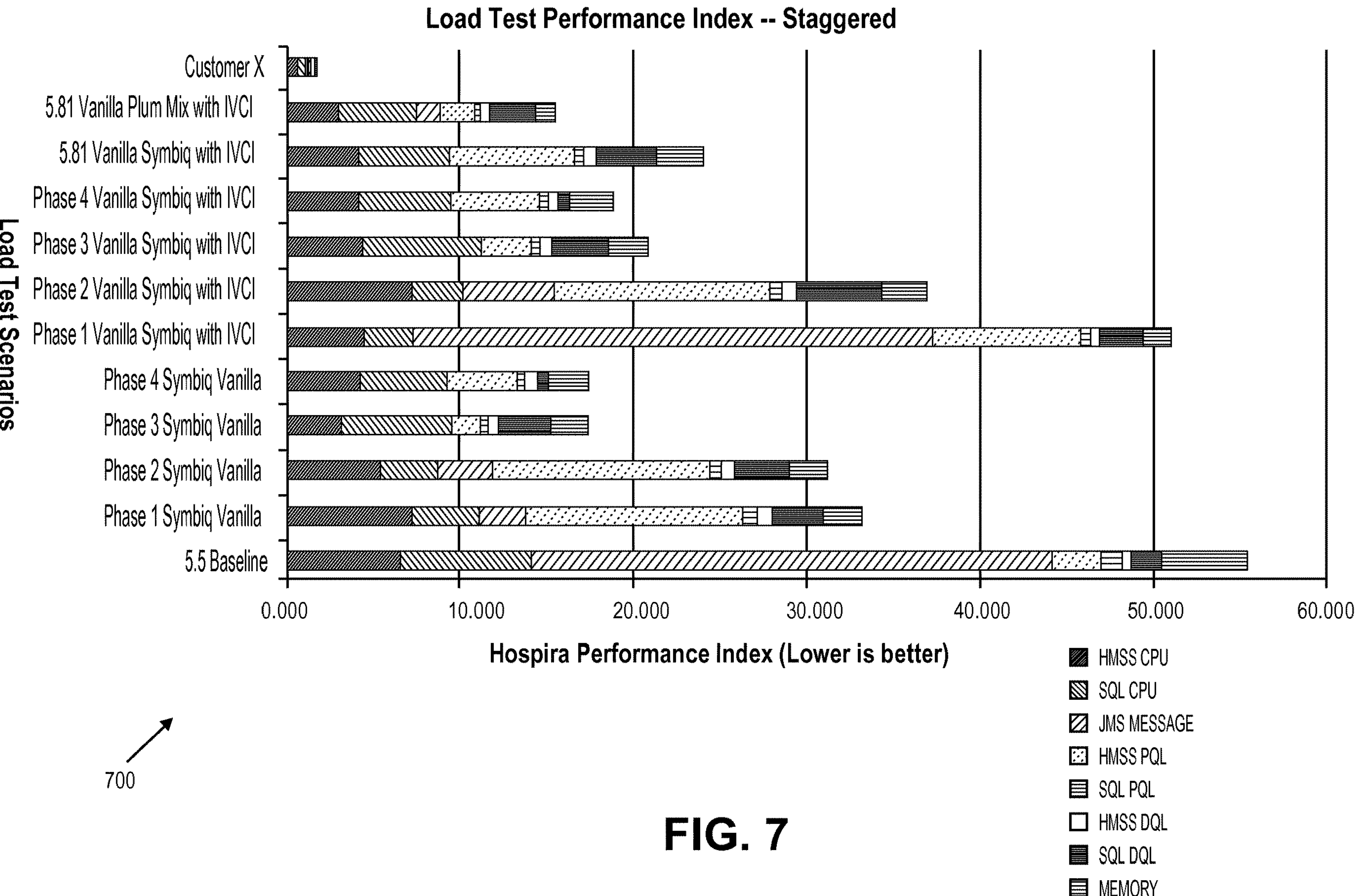
FIG. 7 provides an exemplary graphical output of a performance index analysis.
Figure 8:
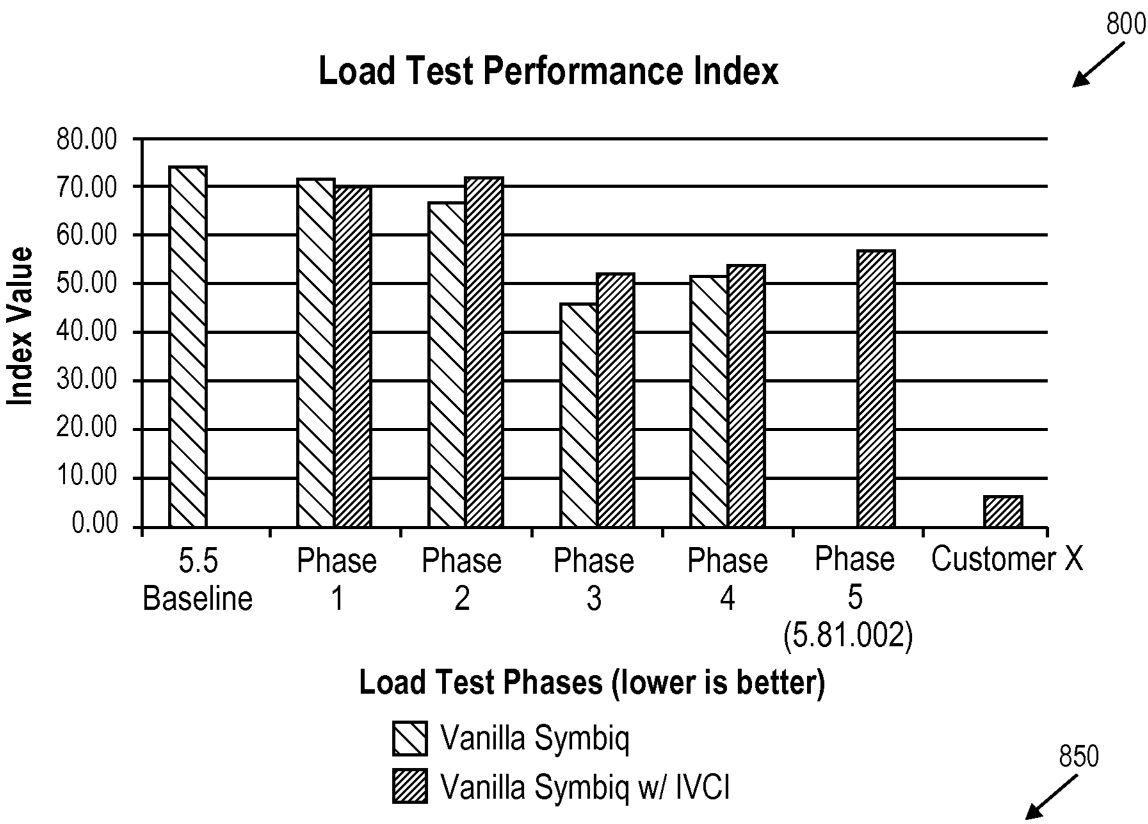
FIG. 8 provides another graphical output with tabular results of a performance index analysis.

FIGS. 7-8 show exemplary outputs generated by the performance index calculations. In FIG. 7, a stacked horizontal bar chart 700 shows relative contributions of various performance factors (HMSS CPU, SQL CPU, etc.), as indicated by the colored segments for each bar. The various bars represent performance component differentiation, such as from different models of infusers. In this sample chart, a comparison of the second and third bars from the top shows that the "5.81 Vanilla Plum Mix with IVCI" (IV with clinical integration) base Plum™ infuser model resulted in better system performance—that is, had a performance index that was smaller in value—than the "5.81 Vanilla Symbiq IVCI" or base Symbig™ infuser model with IVCI. Looking at the sub-segments of these bars, it can be seen that the purple "HMSS PQL" component was a primary contributor to the worsened performance of the "Vanilla" Symbig™ infuser with IVCI compared with the "Vanilla" Plum™ infuser Mix with IVCI. Consequently, a user could use these results to target how to improve processor queue length of the medical device management software (HMSS) when using the Vanilla Symbiq infuser model.

In FIG. 8, another graphical output is presented as a vertical bar chart 800 showing comparison of execution between functional differentiations; that is, between system configurations. For example, phases 1-5 represent changes made within the Hospira MedNet™ system, and the side-by-side bars of chart 800 show comparisons of the base or Vanilla Symbig™ infuser with and without IVCI when run with the different phases. As can be seen, Vanilla Symbig™ infuser with IVCI (blue bars) had higher performance index values and thus worse performance than Vanilla Symbig™ infuser without IVCI (red bars). Table 850 shows the generated output in a numerical format, corresponding to the graphical output of chart 800.

Thus, FIGS. 7-8 show the ability of the performance index to evaluate the effect of different medical devices or management software configurations on the overall performance of a medical device network system. In other embodiments, the performance index could be used to compare different host configurations, with hardware and/or software adjustments. The various outputs may be displayed in different forms viewable by the user, such as, but not limited to graphical displays, numerical listings or tables, or text descriptions. The outputs may be generated as, for example, computer files, printed data, and/or displays on a computer monitor.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those of ordinary skill in the art, without departing from the scope of the present invention. Furthermore, those of ordinary skill in the art will appreciate that the foregoing description is by way of example only, and is not intended to limit the invention. Thus, it is intended that the present subject matter covers such modifications and variations.

What is claimed is:

1. A system comprising:

computer-readable memory storing executable instructions; and one or more processors in communication with the computer-readable memory, and a server, wherein the server is configured to communicate over an infusion pump network with a plurality of infusion pumps to transmit and receive pump messages, and wherein the one or more processors are programmed by the executable instructions to:

monitor transmission or receipt of the pump messages between the server and the plurality of infusion pumps;

identify a plurality of performance parameters, wherein the plurality of performance parameters comprises at least a first performance parameter and a second performance parameter, wherein the first performance parameter comprises a number of messages from the plurality of infusion pumps waiting to be processed;

determine a weighting factor for each of the plurality of performance parameters, wherein each weighting factor is determined based at least in part on a degree to which a corresponding performance parameter contributes to performance of the infusion pump network, wherein a first weighting factor for the first performance parameter is larger than a second weighting factor for the second performance parameter, wherein the second weighting factor is larger than zero; and generate a performance index based at least in part on the plurality of performance parameters and the plurality of weighting factors, wherein the performance index comprises a product of: (a) a maximum index value and (b) a sum of each performance parameter value divided by a corresponding maximum allowed performance parameter value and multiplied by the corresponding weighting factor.

2. The system of claim 1, wherein a largest weighting factor of the plurality of weighting factors corresponds to the first weighting factor of the first performance parameter.

3. The system of claim 1, further comprising a database server configured to store the pump messages, wherein the plurality of performance parameters further comprises a central processing unit (CPU) consumption of the server, a CPU consumption of the database server, a processor queue length (PQL) of the server, a PQL of the database server, a disk queue length (DQL) of the server, a DQL of the database server, or a memory usage.

4. The system of claim 3, wherein a largest weighting factor of the plurality of weighting factors corresponds to the first weighting factor of the first performance parameter, a second largest weighting factor corresponds to the second weighting factor of the second performance parameter, wherein the second performance parameter comprises one or more of the CPU consumption of the server, the CPU consumption of the database server, the PQL of the server, or the PQL of the database server, and a smallest weighting factor corresponds to at least one of the DQL of the server, the DQL of the database server, or the memory usage.

5. The system of claim 4, wherein:

a corresponding maximum allowed performance parameter value of the CPU consumption of the server corresponds to a sum of a maximum of the CPU consumption of the server and a maximum of average CPU consumption of the server, a corresponding maximum allowed performance parameter value of the CPU consumption of the database server corresponds to a sum of a maximum of the CPU consumption of the database server and a maximum of average CPU consumption of the database server, a corresponding maximum allowed performance parameter value of the PQL of the server is based upon a number of cores of the server, a corresponding maximum allowed performance parameter value of the DQL of the server corresponds to a maximum DQL, a corresponding maximum allowed performance parameter value of the number of messages waiting to be processed corresponds to a maximum number of messages waiting to be processed by the plurality of infusion pumps, and a corresponding maximum allowed performance value parameter of the memory usage corresponds to a maximum of the memory usage.

6. The system of claim 3, wherein:

the first weighting factor for the first performance parameter is about 30%;

the second weighting factor for the second performance parameter comprising the CPU consumption for the server is about 12.5%;

a third weighting factor for a third performance parameter comprising the PQL for the server is about 12.5%;

a fourth weighting factor for a fourth performance parameter comprising the DQL for the server is about 5%;

a fifth weighting factor for a fifth performance parameter comprising the CPU consumption for the database server is about 12.5%;

a sixth weighting factor for a sixth performance parameter comprising the PQL for the database server is about 12.5%;

a seventh weighting factor for a seventh performance parameter comprising the DQL for the database server is about 5%; and an eighth weighting factor for an eighth performance parameter comprising the memory usage is about 10%.

7. The system of claim 1, wherein the one or more processors is further configured to simulate a number of infusion pumps communicating with the server to simulate a load on the system and determine performance of the system based on the number of infusion pumps.

8. The system of claim 1, wherein the one or more processors is further configured to determine an optimal number of infusion pumps for the system to achieve a desired system load or speed or an indication of an optimal configuration of the system to achieve the desired system load or speed.

9. The system of claim 1, wherein the one or more processors is further configured to simulate a number of infusion pumps, types of infusion pumps, and a number of messages generated by the number of infusion pumps to determine a load on the system and determine performance of the system.

10. The system of claim 1, wherein the one or more processors are programmed by the executable instructions to cause a display to display an indication of the performance index, wherein the indication of the performance index identifies a relative contribution of each of the plurality of performance parameters to the performance index.

11. A computer-implemented method comprising:

monitoring, using a one or more hardware processors in communication with a server, communications over an infusion pump network between a plurality of infusion pumps and the server, wherein the server is configured to transmit or receive pump messages corresponding to the plurality of infusion pumps, identifying, using the one or more hardware processors, a plurality of performance parameters, wherein the plurality of performance parameters comprises at least a first performance parameter and a second performance parameter, wherein the first performance parameter comprises a number of messages from the plurality of infusion pumps waiting to be processed, determining, using the one or more hardware processors, a weighting factor for each of the plurality of performance parameters, wherein each weighting factor is determined based at least in part on a degree to which a corresponding performance parameter contributes to performance of the infusion pump network, wherein a first weighting factor for the first performance parameter is larger than a second weighting factor for the second performance parameter, wherein the second weighting factor is larger than zero; and generating, using the one or more hardware processors, a performance index based at least in part on the plurality of performance parameters and the plurality of weighting factors, wherein the performance index comprises a product of (a) a maximum index value and (b) a sum of each performance parameter value divided by a corresponding maximum allowed performance parameter value and multiplied by the corresponding weighting factor.

12. The method of claim 11, wherein a largest weighting factor of the plurality of weighting factors corresponds to the first weighting factor of the first performance parameter.

13. The method of claim 12, further comprising simulating, using the one or more hardware processors, a number of infusion pumps communicating with the server to simulate a load on the infusion pump network and determine performance of the infusion pump network based on the number of infusion pumps.

14. The method of claim 12, further comprising determining, using the one or more hardware processors, an optimal number of infusion pumps to achieve a desired system load or speed or an indication of an optimal configuration of the infusion pump network to achieve the desired system load or speed.

15. The method of claim 12, further comprising simulating a number of infusion pumps, types of infusion pumps, and a number of messages generated by the number of infusion pumps to determine a load on the infusion pump network and determine performance of the infusion pump network.

16. The method of claim 11, wherein the server is in communication with a database server that is configured to store the pump messages, wherein the plurality of performance parameters further comprises a central processing unit (CPU) consumption of the server, a CPU consumption of the database server, a processor queue length (PQL) of the server, a PQL of the database server, a disk queue length (DQL) of the server, a DQL of the database server, or a memory usage.

17. The method of claim 16, wherein a largest weighting factor of the plurality of weighting factors corresponds to the first weighting factor of the first performance parameter, a second largest weighting factor corresponds to the second weighting factor of the second performance parameter, wherein the second performance parameter comprises one or more of the CPU consumption of the server, the CPU consumption of the database server, the PQL of the server, or the PQL of the database server, and a smallest weighting factor corresponds to at least one of the DQL of the server, the DQL of the database server, or the memory usage.

18. The method of claim 17, wherein:

the first weighting factor for the first performance parameter is about 30%;

the second weighting factor for the second performance parameter comprising the CPU consumption for the server is about 12.5%;

a third weighting factor for a third performance parameter comprising the PQL for the server is about 12.5%;

a fourth weighting factor for a fourth performance parameter comprising the DQL for the server is about 5%;

a fifth weighting factor for a fifth performance parameter comprising the CPU consumption for the database server is about 12.5%;

a sixth weighting factor for a sixth performance parameter comprising the PQL for the database server is about 12.5%;

a seventh weighting factor for a seventh performance parameter comprising the DQL for the database server is about 5%; and an eighth weighting factor for an eighth performance parameter comprising the memory usage is about 10%.

19. The method of claim 17, wherein:

a corresponding maximum allowed performance parameter value of the CPU consumption of the server corresponds to a sum of a maximum of the CPU consumption of the server and a maximum of average CPU consumption of the server, a corresponding maximum allowed performance parameter value of the CPU consumption of the database server corresponds to a sum of a maximum of the CPU consumption of the database server and a maximum of average CPU consumption of the database server, a corresponding maximum allowed performance parameter value of the PQL of the server is based upon a number of cores of the server, a corresponding maximum allowed performance parameter value of the DQL of the server corresponds to a maximum DQL, a corresponding maximum allowed performance parameter value of the number of messages waiting to be processed corresponds to a maximum number of messages waiting to be processed by the plurality of infusion pumps, and a corresponding maximum allowed performance value parameter of the memory usage corresponds to a maximum of the memory usage.

20. The method of claim 16, further comprising causing a display to display an indication of the performance index, wherein the indication of the performance index identifies a relative contribution of each of the plurality of performance parameters to the performance index.

* * * * *